US008157146B2

(12) United States Patent
Edoga et al.

(10) Patent No.: US 8,157,146 B2
(45) Date of Patent: Apr. 17, 2012

(54) STAPLING DEVICE

(75) Inventors: John K. Edoga, North Beach, NJ (US); Thierry Richard, Florham Park, NJ (US); Peter Hinchliffe, Campbell Hall, NY (US)

(73) Assignee: Edrich Health Technologies, Inc., Morristown, NJ (US)

( * ) Notice: Subject to any disclaimer, the term of this patent is extended or adjusted under 35 U.S.C. 154(b) by 450 days.

(21) Appl. No.: 12/093,637

(22) PCT Filed: Nov. 16, 2006

(86) PCT No.: PCT/US2006/044653
§ 371 (c)(1),
(2), (4) Date: Dec. 15, 2008

(87) PCT Pub. No.: WO2007/059304
PCT Pub. Date: May 24, 2007

(65) Prior Publication Data
US 2009/0114233 A1 May 7, 2009

Related U.S. Application Data

(60) Provisional application No. 60/737,274, filed on Nov. 16, 2005, provisional application No. 60/749,764, filed on Dec. 13, 2005.

(51) Int. Cl.
*A61B 19/00* (2006.01)
*A61B 17/10* (2006.01)
(52) U.S. Cl. ....... 227/175.1; 227/19; 606/139; 606/143; 606/159; 606/151; 604/96.01; 604/103; 623/1.11; 623/1.23

(58) Field of Classification Search ............... 227/175.1, 227/19; 606/139, 143, 159, 151; 623/1.23, 623/1.11; 604/96.01, 103
See application file for complete search history.

(56) References Cited

U.S. PATENT DOCUMENTS

| 4,595,007 A | * | 6/1986 | Mericle ........................ 606/221 |
| 4,872,874 A | * | 10/1989 | Taheri .......................... 128/898 |
| 5,104,399 A | | 4/1992 | Lazarus |
| 5,695,504 A | | 12/1997 | Gifford, III et al. |
| 5,720,755 A | * | 2/1998 | Dakov ......................... 606/139 |
| 5,746,766 A | | 5/1998 | Edoga |
| 5,829,447 A | * | 11/1998 | Stevens et al. ............... 128/898 |
| 5,843,169 A | * | 12/1998 | Taheri .......................... 623/1.11 |
| 5,911,733 A | * | 6/1999 | Parodi ......................... 623/1.15 |
| 5,954,764 A | | 9/1999 | Parodi |
| 5,968,053 A | * | 10/1999 | Revelas ....................... 606/108 |

(Continued)

FOREIGN PATENT DOCUMENTS
WO WO02085254 * 10/2002 .................. 623/1.36

*Primary Examiner* — Thanh K Truong
*Assistant Examiner* — Michelle Lopez
(74) *Attorney, Agent, or Firm* — Day Pitney LLP

(57) ABSTRACT

An endovascular stapler (100) for securing an endograft to a vessel is disclosed. The stapler has a staple housing (104), an actuating mechanism (148) and an expansion mechanism (126). The staple housing (104) has a plurality of staple cartridges (128) adapted for storing at least one staple (180) therein. The staple cartridges (128) have an exit area (130) for discharging at least one of the staples (180) therethrough. The actuating assembly (148) is adapted for actuating the plurality of staple cartridges (128) to discharge the at least one staple through the exit area. The expansion mechanism (126) is in operative association with staple cartridges (128). The expansion mechanism (126) is operative for pushing the exit area (130) against the endograft when discharging the at least one staple therethrough.

30 Claims, 31 Drawing Sheets

U.S. PATENT DOCUMENTS

| | | |
|---|---|---|
| 6,022,372 A | 2/2000 | Kontos |
| 6,042,607 A * | 3/2000 | Williamson et al. .......... 623/2.11 |
| 6,149,660 A * | 11/2000 | Laufer et al. .................. 606/143 |
| 6,221,043 B1 * | 4/2001 | Fischell et al. ........... 604/103.07 |
| 6,328,727 B1 * | 12/2001 | Frazier et al. ................. 604/500 |
| 6,416,522 B1 * | 7/2002 | Strecker ........................ 606/143 |
| 6,776,784 B2 * | 8/2004 | Ginn ............................. 606/151 |
| 7,351,258 B2 * | 4/2008 | Ricotta et al. ................ 623/1.36 |
| RE40,377 E * | 6/2008 | Williamson et al. ......... 623/2.11 |
| 7,954,688 B2 * | 6/2011 | Argentine et al. ......... 227/176.1 |

* cited by examiner

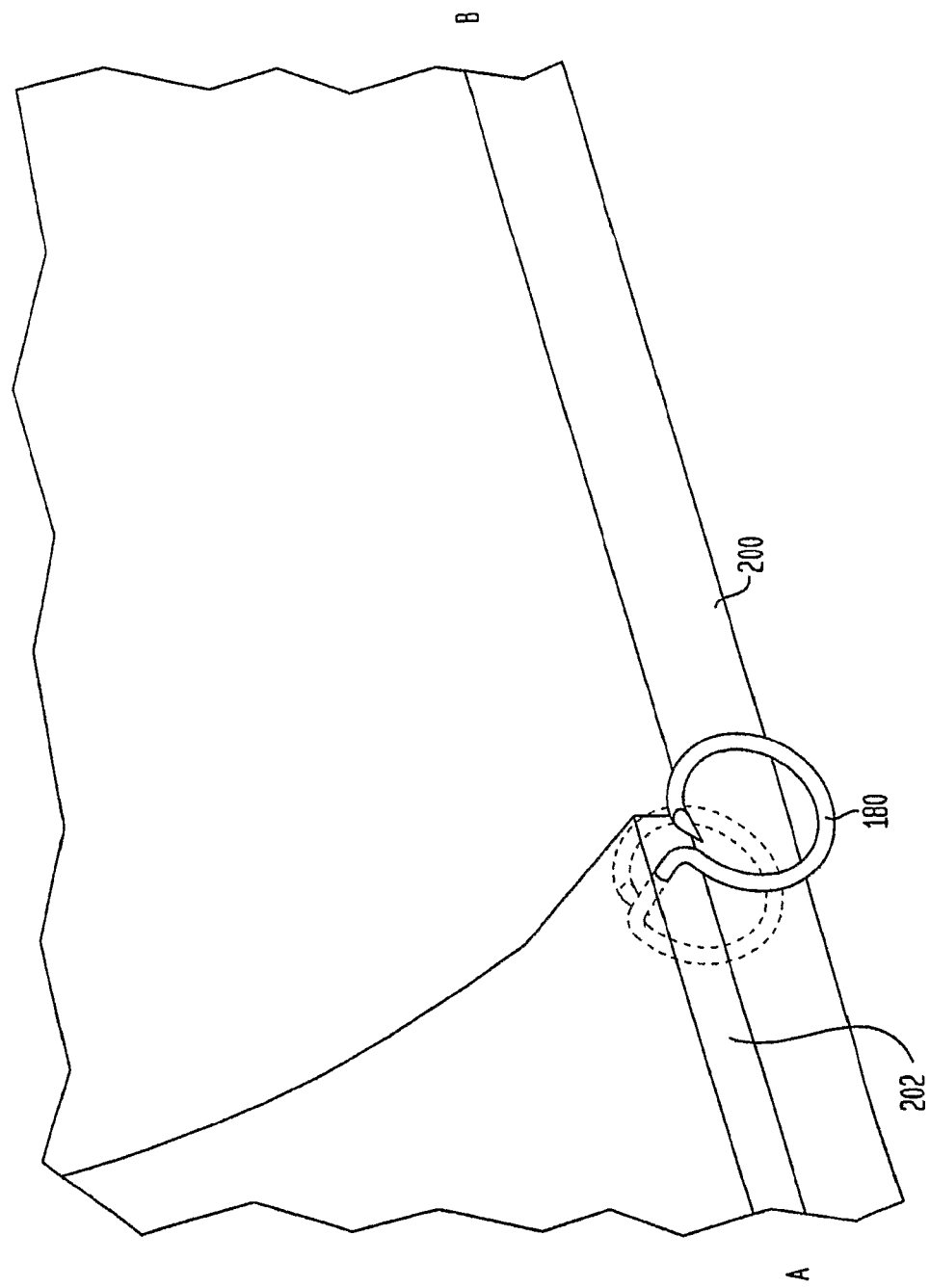

STAPLING DEVICE

CROSS-REFERENCE TO RELATED APPLICATIONS

This application claims the benefit of the filing date of U.S. Provisional Patent Application Ser. No. 60/737,274 filed Nov. 16, 2005, and U.S. Provisional Patent Application Ser. No. 60/749,764 filed Dec. 13, 2005, the disclosures of which are hereby incorporated herein by reference.

BACKGROUND OF THE INVENTION

It is well known that endovascular endografts may be inserted into the human body during numerous medical procedures. Endografts are typically inserted into vessels and held in place by friction, such as with self-expanding or balloon expandable stents. The endografts may also be affixed to vessels with hooks, barbs or staples.

The endografts may be formed from synthetic materials, such as polyester, expanded polytetraflouroethylene ("ePTFE"), or others. The endografts may also be formed of natural vessels harvested from other areas of the body or from a donor mammal. Notwithstanding the various materials utilized, migration of the endografts over time remains a problem.

Caudad device migration, which refers to movement of an endograft away from the heart of a person, is known to lead to a Type 1 endoleak with aneurysm sac reperfusion, enlargement and rupture. Cephalad device migration, which refers to movement of an endograft toward the heart of a person, may lead to coverage of the renal artery orifices and renal insufficiency.

Such device migration is caused by many factors. One known factor is poor patient selection. Patients with cone shaped aortic necks, severe neck angulation, short necks or whose aortic necks have laminated thrombus present at the landing site are generally susceptible to device migration problems. Other device migration issues are caused by changing aortic morphology following device implantation including continuing aortic neck growth. Finally, migration may be caused by device structural fatigue and device design related issues. Device migration has been found even in cases in which these identified conditions do not exist.

Treatment of caudad migrations have traditionally been conducted by the addition of "sleeves" to the proximal end of the endograft in an effort to regain purchase between the endograft and the vessel to which it is attached in order to maintain a seal between the two. More drastic options include resorting to conventional surgery. These late conversions are, unfortunately, associated with an unacceptably high mortality rate.

Treatment options for the cephalad migrations are even less attractive. In the face of continued migration, resignation may be the only option as such migration may lead to renal insufficiency requiring hemodialysis. To permit device removal, a typical conversion in this case involves supraceliac aortic cross-clamping, and its associated problems.

Prior attempts at fixation of migrating devices, including additions of hooks, barbs, supra renal stents and other fastening devices have proven to be insufficient. Some conventional endovascular stapling devices have been described which fire or discharge one staple at a time requiring removal and reinsertion or repositioning of the devices multiple times to secure an endograft to a vessel. It would therefore be advantageous to provide an endovascular stapling device which may be used to adequately arrest existing migrations, as well as secure new endografts in a manner likely to eliminate future migration. Actual fixation of the endograft to the aortic neck with closed staples at multiple points will also prevent the aorta itself from enlarging as the aorta is forced to conform to a prosthetic graft with a predetermined maximum diameter.

SUMMARY OF THE INVENTION

The endovascular stapler of the present invention is designed to overcome the deficiencies of the prior art. In one embodiment, the endovascular stapler is capable of discharging a plurality of staples simultaneously. The stapler includes an expansion mechanism which is located at the distal end of the stapler and comprises a plurality of strut members arranged in a cage structure. Each strut member includes a staple cartridge which houses one or more staples where the staples are oriented along a longitudinal axis of the stapler. The stapler may include a displacement mechanism such as a non-occlusive balloon disposed within the confines of the cage structure. The stapler has a catheter portion which extends proximally from the cage structure to a trigger or actuating handle which is outside the patient's body during use. The catheter portion comprises channels which house a guide wire, an actuating mechanism for actuating the expansion mechanism, an actuating mechanism for causing staples to be discharged from the staple cartridges, and an inflation channel for inflating/deflating the non-occlusive balloon. The actuating mechanisms may be composed of wires which can pull the components of the stapler or rods which can pull other members into the desired configuration or position. The actuating mechanisms may also be hydraulic in nature employing various fluids and gases. The non-occlusive balloon may be configured as separate segments with each segment being associated with a strut member of the cage structure. The outer wall of each balloon segment may be permanently fixed to the inside surface of the corresponding strut member. The balloon segments may be in fluid communication with the balloon inflation channel as well as with each other in order to assure uniform pressurization of the balloon and equal pressure application on the strut members when the balloon is inflated.

In one aspect of the present application, disclosed is an endovascular stapler for securing an endograft to a vessel. The endovascular stapler includes a staple housing, an actuating mechanism and an expansion mechanism. The staple housing includes a plurality of staple cartridges adapted for storing at least one staple therein. The staple cartridge has an exit area for discharge of the at least one staple therethrough. The actuating assembly is adapted for actuating the plurality of staple cartridges for discharging the at least one staple through the exit area. The expansion mechanism is in operative association with the plurality of staple cartridges. The expansion mechanism is operative for pushing the exit area against the endograft when discharging the at least one staple therethrough.

In one or more embodiments, the endovascular stapler of the present application may include the following features. The expansion mechanism may comprise a plurality of expandable portions including strut members configured to form an expandable cage structure. Each strut member may include a plurality of strut segments each coupled to each other using a hinge mechanism. The hinge mechanism may be a living hinge. The strut member may be coupled to a staple housing and a staple cartridge. The expandable portions may be adapted to expand outwardly away from a longitudinal axis of the stapler.

The expandable portions may be adapted to retract inwardly toward a longitudinal axis of the stapler. The staple cartridges may be adapted to be actuated in a substantially simultaneous manner. The staple cartridges may be adapted to be actuated in a sequential manner, with one staple cartridge being actuated after another staple cartridge being actuated.

The actuating assembly may include a pusher and a trigger where the pusher is adapted to be advanced by the trigger to discharge the at least one staple. The pusher may advance the at least one staple in a direction opposite to a distal end of the staple housing. The plurality of staple cartridges may include a plurality of staples therein. The staples may be arranged in a tandem manner. The staples may be deformed prior to exiting the exit area.

The stapler may include a displacement mechanism in operative association with the plurality of staple cartridges, wherein the displacement mechanism is operative for pushing the staple cartridges against said endograft. The displacement mechanism may include a balloon positioned to exert pressure on the staple cartridges. The balloon may be adapted to be selectively inflated and deflated. The balloon may be a partially compliant balloon. At least a portion of the balloon may be disposed within an interior of the staple housing. The balloon may include a plurality of segments wherein at least one of the segments is operatively coupled to at least one of the plurality of staple cartridges. At least one of the segments may be in fluid communication with at least another of the segments. At least one of the segments may be adapted to engage at least a portion of the endograft. At least one of the segments may be attached to a surface opposite the exit area of at least one of the plurality of staple cartridges. The segments may be spaced apart to provide at least one opening therebetween. The opening may be adapted to allow flow of a fluid or gas therethrough. The displacement mechanism may comprise a stent. The stent may be adapted to expand outwardly away from a longitudinal axis of the stapler. The stent may be adapted to retract inwardly toward a longitudinal axis of the stapler.

In another aspect of the present application, disclosed is a method of attaching an endograft to a vessel wall with an endovascular stapler. The stapler has a staple housing with a plurality of staple cartridges. The staple cartridges are adapted for storing at least one staple therein, and the staple cartridges have an exit area for discharging the at least one staple therethrough. The method includes inserting the staple housing into the endograft, actuating the plurality of staple cartridges so to push the staple exit areas against the endograft, and actuating the plurality of staple cartridges so to discharge the at least one staple through the exit areas and into the endograft and the vessel.

BRIEF DESCRIPTION OF THE DRAWINGS

The subject matter regarded as the invention is particularly pointed out and distinctly claimed in the concluding portion of the specification. The invention, however, both as to organization and method of operation, together with features, objects, and advantages thereof will be or become apparent to one with skill in the art upon reference to the following detailed description when read with the accompanying drawings. It is intended that any additional organizations, methods of operation, features, objects or advantages ascertained by one skilled in the art be included within this description, be within the scope of the present invention, and be protected by the accompanying claims.

In regard to the drawings,

FIG. 16 depicts a cut-away view of the fully formed staple discharged into an endograft and a vessel wall of FIG. 15.

FIG. 19 depicts a cut-away view of a staple cartridge during a further step of firing the staple of FIG. 17a.

FIG. 20 depicts a cut-away view of a staple cartridge during a still further step of firing the staple of FIG. 17a.

DETAILED DESCRIPTION

Figure 1:
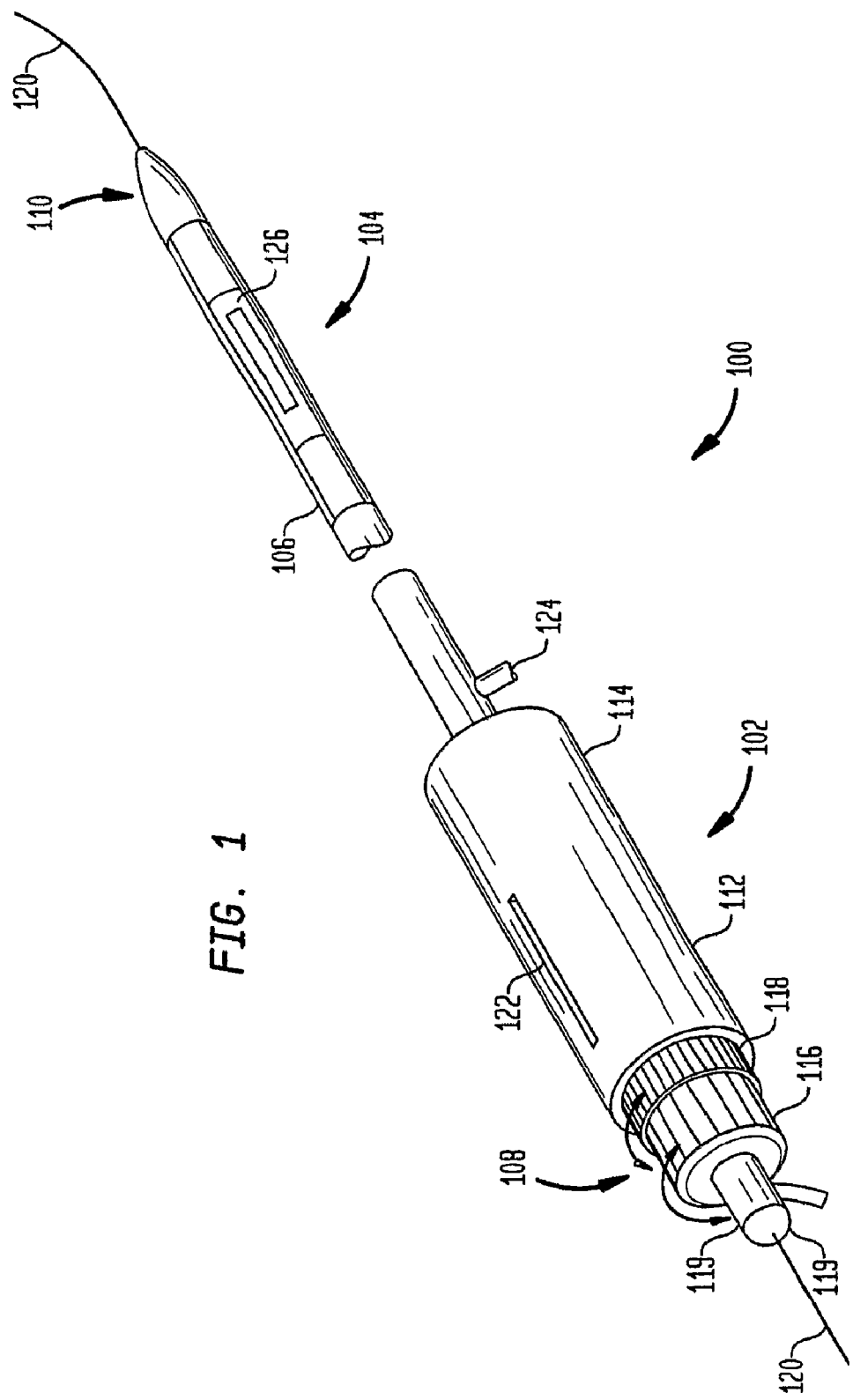
FIG. 1 is a perspective view of an endovascular stapler in accordance with one embodiment of the present application.

In the following is described the preferred embodiments of the endovascular stapler of the present invention. In describing the embodiments illustrated in the drawings, specific terminology will be used for the sake of clarity. However, the invention is not intended to be limited to the specific terms so selected, and it is to be understood that each specific term includes all technical equivalents that operate in a similar manner to accomplish a similar purpose.

In general, the endovascular stapler is a device which includes a stapling portion, or staple housing, intended to be inserted into the human body of a patient through a vessel, such as and without limitations, an artery and apposed against a vessel wall, such as an arterial wall, or an endograft deployed within a vessel. In order to place the staple housing in this position, an expansion mechanism having multiple expandable portions which contain the staple cartridges can be used to expand outward to appose against the vessel wall. In one embodiment, the expansion mechanism comprises a plurality of strut members forming a cage structure. Each of the strut members supports a staple cartridge. In order to further expand this mechanism and apply more pressure to the strut members housing the staple cartridges and maintain this position of firm apposition to the inside surface of the endograft and vessel wall during the firing of the staples, a displacement device can be added, such as a balloon, and inflated inside the cage structure to further push and hold the stapling portion against the vessel wall or endograft. In one embodiment, the balloon is disposed within the staple housing and configured to be non-occlusive. Preferably, the displacement device is a partially compliant balloon. Other expansion and displacement mechanisms, such as stents, may also be utilized. In a practical and preferred embodiment, the staple housing is capable of discharging at least a plurality of staples during a single step (one from staple cartridge at a strut member) or discharge application without the need to reposition the staple housing. The staples can be discharged at the same time in a substantially simultaneous manner or one after another in a sequential manner or in any desired pattern. In one embodiment, a staple cartridge is disposed on each of the expandable portions of the expansion mechanism. The staple cartridges can store multiple staples and include a staple exit area through which the staples can be discharged. In this manner, multiple staples can be discharged from each cartridge without the need to remove and reinsert the stapler, which reduces the necessary time to perform a surgical procedure. In order to repeat the process, the balloon is deflated, the expansion mechanism (e.g., cage structure) is partially collapsed, the stapler is rotated to a new location (e.g., a rotated a number of degrees) and another set of staples is discharged.

The expandable portions may be expanded to appose the endograft and vessel wall by actuating a trigger located on the handle of the endovascular stapler, which remains outside of the patient's body. In one embodiment, the balloon can be inflated to further displace the expandable portions to provide a more firm contact with the endograft and/or the vessel wall. In another embodiment, the balloon may contact the endograft or vessel directly opposite to the site into which staples will be displaced to enhance firm contact by the staple cartridges on the endograft and vessel. The staples may then be advanced through the vessel wall and endograft by actuating a trigger. The staple may be either preformed with the same initial curvature or it may be flat. Either way, the staple cartridge typically includes a conforming element to curve the staple or control the rate at which the preformed staple returns to its default shape as it advances. The staple will then penetrate the endograft and the vessel wall and will curve in a predictable path such that its leading edge loops back, possibly repenetrating the exterior of the vessel wall and endograft, thus holding the vessel wall and the endograft against each other.

The endovascular stapler of the present invention may be an "over the wire" device designed to fit through a typical sheath for aortic and iliac arterial use, such as a 16 French or larger sheath. It is also possible that the stapler may be miniaturized to fit through smaller sheaths for fixation of endografts in smaller caliber vessels. The stapler is generally introduced through a sheath inserted into the femoral artery or other suitable access into the lumen of an endograft. Its leading elements are advanced to the proximal end of the endograft which should be accurately identified. An endograft can have clearly visible markers at their proximal ends. Identification of the endograft ends may also be achieved by utilizing an endovascular ultrasonic probe or by an externally applied duplex ultrasound. In one embodiment, the end portion of an endograft fabric may be boldly marked with radio opaque thread. In other embodiments, radiologic techniques such as road mapping may be used to locate the ends of the endograft. As is known in the art, multiple guide wires may be used during the surgical procedure.

When the staple housing of the stapler is aligned with the proximal end of the endograft, the staple cartridges may be forcibly abutted against the endograft and/or vessel wall by expansion of the expandable portions and inflation of a preferably partially compliant balloon. In this position, in a preferred embodiment, a single actuation of a single trigger mechanism preferably causes displacement of multiple staples through the endograft and vessel wall. Following the deployment of a first set of multiple staples during a single discharge application, the balloon may be partially deflated, the expandable cage partially collapsed, the stapler rotated, and the process repeated to deploy a second set of staples and so on.

In other embodiments, the endovascular stapler may include a collet type expansion structure such that the stapler may be inserted into the vessel in a retracted position and then expanded radially by a balloon or other mechanism to fill the vessel void. In other embodiments, anvil-less staples, or self-forming staples typically made of Nitinol, may then be fired from the device to secure an endograft to the vessel. Such staples may improve upon the stapler's minimally invasive advantages. The endograft may include a flexible ring or stent at its proximal end for initial apposition of the endograft to the vessel prior to staple firing. In preferred embodiments, the anvil-less staple may be fired at an angle approximately ninety degrees to the device. The device may also include mechanisms to capture an endograft during insertion of the device, where the endograft is then released upon firing of the staples.

Referring to the figures, FIG. 1 depicts an endovascular stapler 100 in accordance with one embodiment of the present invention. As is shown, the stapler 100 may comprise a trigger housing or handle 102 located at the proximal end 108 of the stapler 100 and a stapling mechanism or housing 104 located at the distal end 110 of the stapler. A catheter 106 provides a connection between the trigger housing 102 and the staple housing 104. The trigger housing 102 may include a first trigger 116 and a second trigger 118 located towards a front portion 112 of the housing 102. The triggers 116, 118 are concentrically arranged and capable of rotating about a longitudinal axis of the trigger housing 102. The first trigger 116 is part of a staple actuation mechanism configured to actuate the discharge of staples from the staple housing 104 as explained below. In one embodiment, the trigger 116 is a dial capable of being turned a predetermined amount, such as ¼ turn, to cause multiple staples to be discharged at the staple housing 104 during a single application. The trigger 116 can be rotated again to discharge a second set of multiple staples. In other embodiments, the trigger 116 can be turned in other increments such as ½ and ¾ turns or other increments. The second trigger 118 is part of an expansion mechanism configured to actuate the expansion and retraction of expandable portions 126 of the stapling mechanism 104 as explained below in further detail. In one embodiment, the second trigger 118 can be a dial capable of being rotated a predetermined amount in a clockwise direction to cause the expandable portions to expand and rotated in a counter-clockwise direction to cause the expandable portions to retract or collapse, or vice-versa.

Other mechanical means can be used as trigger or actuating elements such as sliders or collars which can be used to perform equivalent functions to those of the dials. The triggers 116, 118 provide a manual means of actuating the various components of the stapling mechanism 104 such as the discharge of multiple staples therefrom. However, it is contemplated that an automatic means of actuating the components of the staple housing can be used. For example, a computer controlled actuator device can be programmed to perform such functions. The trigger housing or handle 102 also can include an indicator 122 which provides a visual indication of the number of staples discharged from each cartridge. The indicator 122 is operatively coupled to the first trigger 116 so to track the rotation of the first trigger and thus the number of staples discharged. In operation, upon sufficient rotation of the first trigger 116 to discharge staples, the indicator 122 increments the number of staples discharged and displays the number through a window on the trigger housing. The trigger 116 can automatically lock following the discharge of a set of staples and may be "rearmed or released" before the next set of staples is fired.

In one embodiment, located at the front 112 of the trigger housing 102 is an input port 119 to allow a guide wire 120 to be inserted therethrough and to exit at the staple housing 104 located at the distal end 110 of the stapler 100. The trigger housing 100 may also include a balloon inflation port 124 located towards the distal portion 114 of the trigger housing 102. As explained in detail below, the staple housing 104 includes a stapling mechanism 104 comprising a plurality of strut members arranged in a cage structure. Each of the strut members contains a staple cartridge with each cartridge holding multiple staples. The strut members and associated staple cartridges are arranged in a radial fashion and are adapted to discharge multiple staples (one staple per strut member) from the staple cartridges in a single discharge actuation or application.

Figure 2:
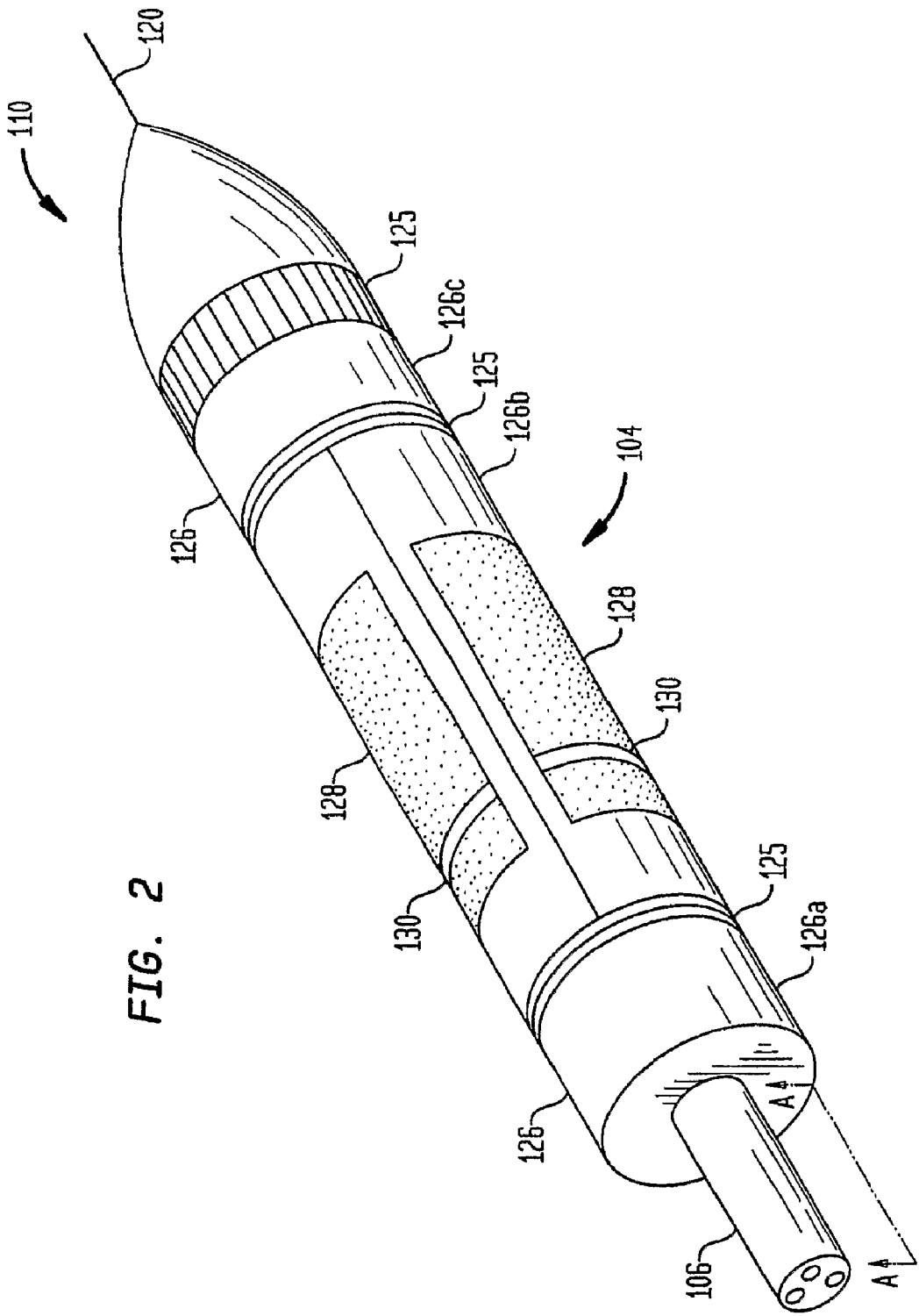
FIG. 2 is a detailed view of a portion of the stapler of FIG. 1 showing a cage structure comprising strut members with each strut member having a staple cartridge, wherein the strut members are shown in the retracted position.
Figure 4:
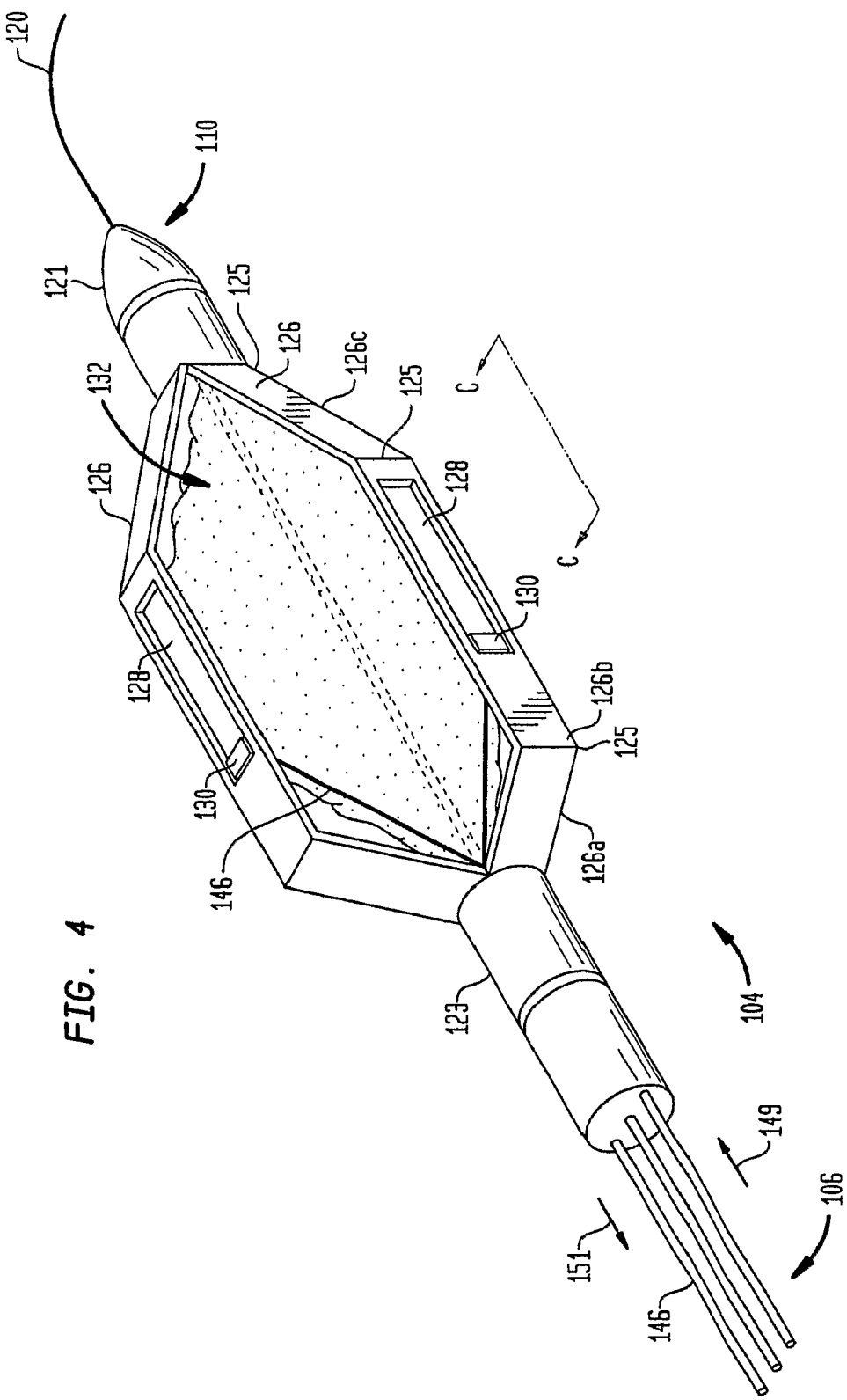
FIG. 4 is a detailed view of a portion of the stapler of FIG. 2 showing the strut members in the expanded position prior to the inflation of the balloon located within the cage structure formed by the strut members.

FIG. 2 shows a detailed view of the staple housing 104 of FIG. 1. The staple housing 104 comprises an expansion mechanism formed from a plurality of expandable portions 126. In one embodiment, the expandable portions are strut members forming a cage structure. In one embodiment, the expandable portions 126 comprise a bottom segment 126a, a middle segment 126b, and a top segment 126c (shown in FIG. 4 in an expanded position), all of which are hingedly coupled to each other using a hinge mechanism 125 to allow flexing inward and outward. In one embodiment, the hinge mechanism 125 is a living hinge as well known in the art. The structure is configured to expand outwardly away from a longitudinal axis of the stapler by parallelogram deformation by bending at the living hinges 125 upon actuation and to retract or collapse inwardly by straightening of the same living hinges to its natural position. Although three segments are shown for each expandable portion 126, it is contemplated that 2 or more than 3 such segments can be used. The expandable portions 126 are shown in a retracted position but are capable of being in an expanded position (FIG. 4). The middle segment 126b of the expandable portions 126 may include a staple cartridge 128 disposed on a portion of an exterior surface of the middle segment. Each staple cartridge 128 is adapted to carry one or more staples and includes a staple exit area 130 through which the staples can be discharged. In addition, a displacement mechanism, such as a balloon 132 (FIGS. 4 and 5), may be disposed within the staple housing 104 and when inflated, helps maintain the expandable portions 126 in the expanded position, pressed firmly against the inside surface of the endograft and vessel as explained in detail later.

Figure 3:
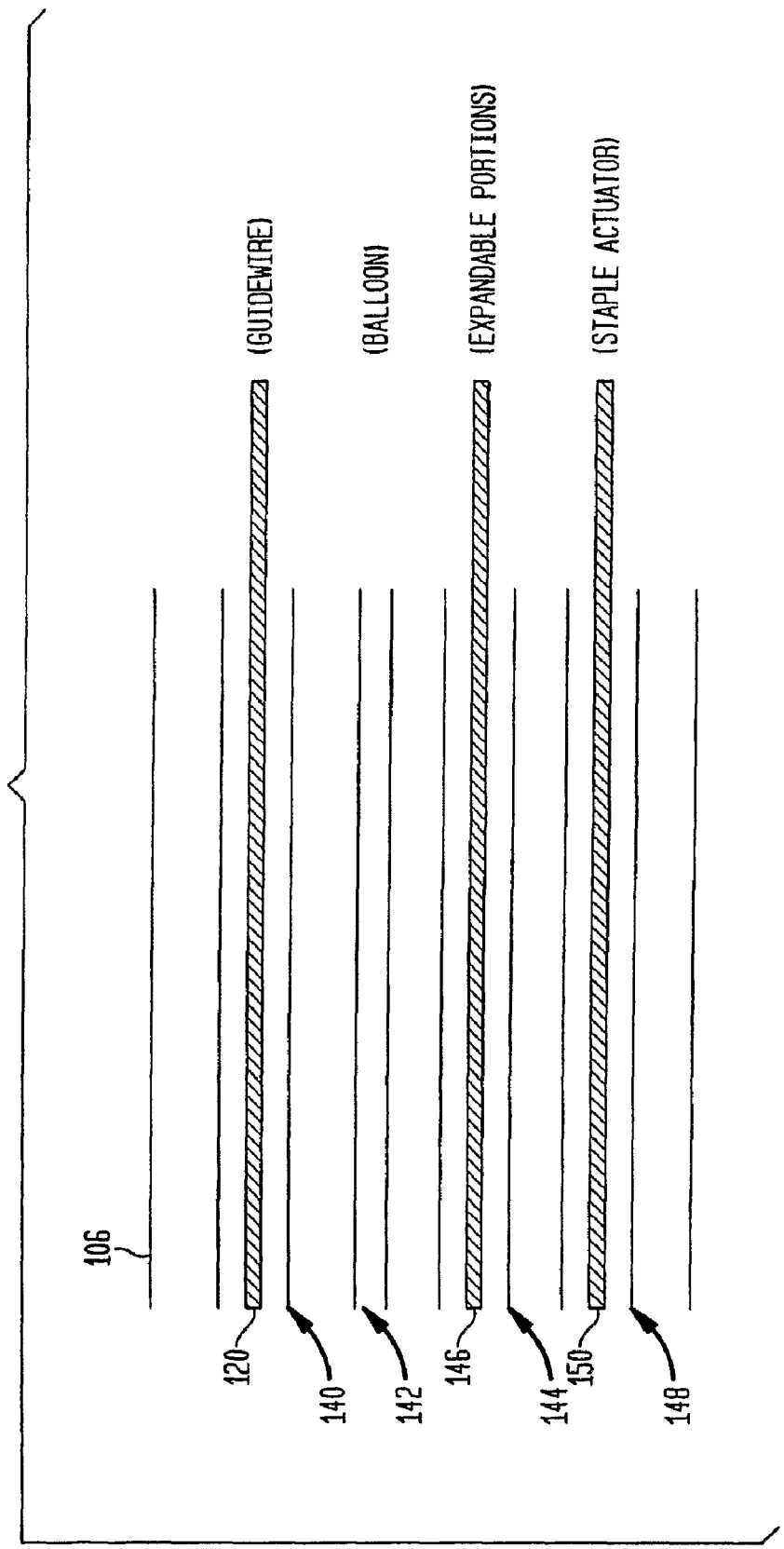
FIG. 3 is a longitudinal sectional view of the catheter of the stapler of FIG. 2 showing the internal components thereof taken along section lines A-A.
Figure 5:
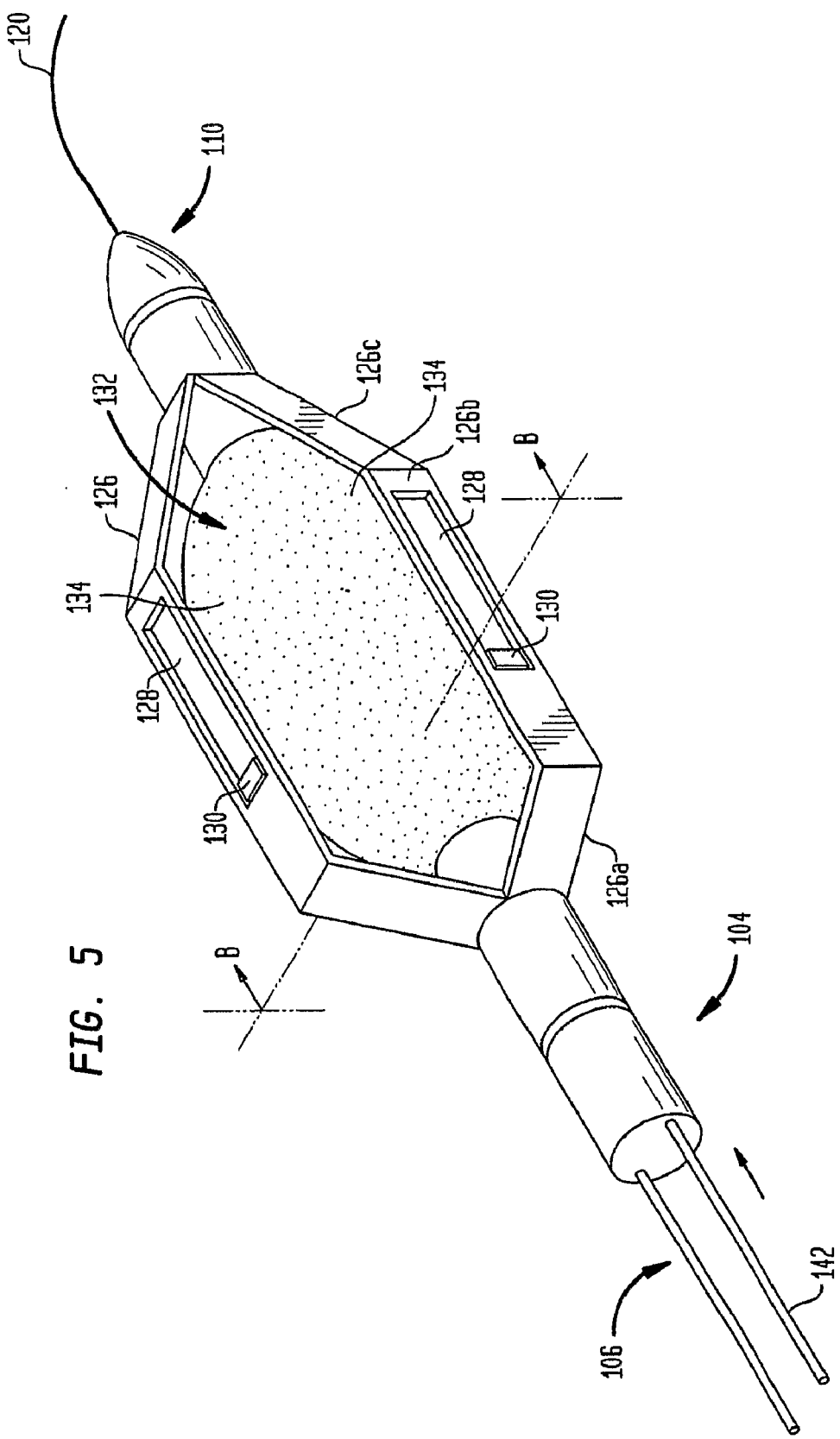
FIG. 5 is a detailed view of the stapler FIG. 4 showing the strut members in the expanded position with the inflated balloon located within the cage structure formed by the strut members.
Figure 7:
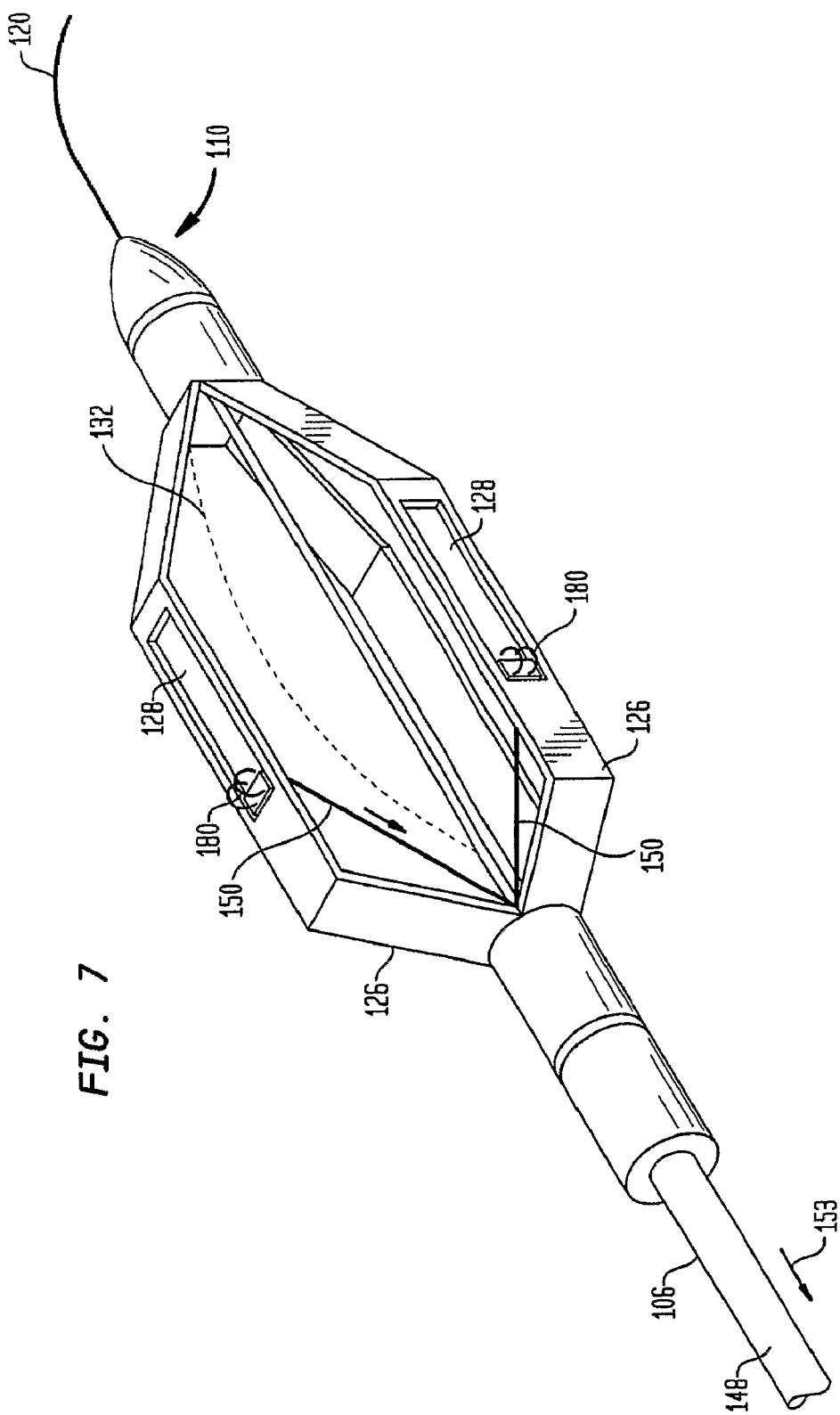
FIG. 7 is a perspective view of the staple housing of FIG. 5 showing staples discharged from staple cartridge.

FIG. 3 depicts a longitudinal sectional view of the catheter 106 of FIGS. 1 and 2. The catheter 106 may include a guide wire channel 140 for carrying the guide wire 120 between the trigger housing 102 and the staple housing 104. The catheter 106 may include an actuator channel 144 for carrying an actuator wire 146 with a proximal end connected to the second trigger 118 of the trigger housing 102 (FIG. 1) and a distal end connected to the expandable portions 126 of the staple housing 104 (FIG. 4). The actuator wire 146 is part of an expansion mechanism for expanding and retracting the expandable portions 126 of the staple housing 104 (FIG. 4 shows the staple housing in an expanded position). The catheter 106 may include a balloon inflation channel 142 with a proximal end connected to the balloon inflation port 124 (FIG. 1) of the trigger housing 102 and a distal end connected to balloon 132 disposed within the staple housing 104. The balloon inflation channel 142 is part of a displacement mechanism used to selectively inflate and deflate the balloon (FIG. 4 shows the balloon 132 deflated and FIG. 5 shows the balloon inflated). The catheter 106 may also include a staple actuator channel 148 for carrying an actuator wire 150 with a proximal end connected to the first trigger 116 of the trigger housing 102 (FIG. 1) and a distal end connected to the staple cartridges 128 of the staple housing (FIG. 7). The actuator wire 150 is part of an actuating mechanism used to discharge staples 180 from the staple cartridges 128 where the staples are used to secure an endograft to a vessel, as best shown in FIG. 7. For example, rotation of the dial 116 causes translation of the corresponding wire (FIG. 1).

FIG. 4 shows a detailed view of an embodiment of the staple housing of FIG. 1 with the expandable portions 126 in an expanded position. The staple housing 104 shows expandable portions 126 with each portion having a staple cartridge 128 and a staple exit area 130. The expandable portions 126 have a proximal portion 123 which is fixed and a distal portion 121 which is free to move along the longitudinal axis of the staple housing 104. As explained above, the actuator wire 146 is part of an expansion mechanism to expand and retract the expandable portions 126. In one embodiment, the staple housing 104 is configured with three expandable portions 126. In other embodiments, the staple housing can be configured with a different number of expandable portions such as two, four, five or six portions. In one embodiment, the wire 146 is configured as single wire within the catheter 106 and extends to three separate wires with a corresponding wire being attached to the interior surface of a middle segment 126b of a corresponding expandable portion 126. The expandable portions 126 are made of a flexible material, such as plastic, and with a tendency to remain in the retracted position as shown FIG. 2.

As explained above, the expandable portions 126 comprise three segments 126a, 126b, 126c all hingedly coupled to each other by means of living hinges so to be capable of expanding and retracting. To expand the expandable portions 126 outward, the wire 146 is urged in a direction, shown by arrow 151, opposite the distal end 110, where such movement causes the expandable portions 126 to expand outwardly away from the longitudinal axis of the staple housing. In one embodiment, the trigger 118 (FIG. 1) of the trigger housing 102 is used to actuate the expansion of the expandable portions outward by rotating the trigger a predetermined amount in a first direction such as clockwise. In the expanded position, the diameter of the staple housing located near the expansion mechanism increases whereas the length of the staple housing decreases. To retract the expandable portions 126 inward, to the position shown in FIG. 2, the wire 146 is urged in a direction, shown by arrow 149, toward the distal end 110, where such movement causes the expandable portions 126 to retract inwardly toward the longitudinal axis of the staple housing. In one embodiment, the trigger 118 (FIG. 1) of the trigger housing 102 is used to actuate the retraction of the expandable portions inward by rotating the trigger a predetermined amount in a second direction such as counterclockwise.

The balloon 132 is disposed within the interior of the staple housing 104 and is shown in a partially deflated condition. In a preferred embodiment, the balloon 132 can be inflated and used to cause expansion of expandable portions 126 to help provide a firm contact between a vessel and an endograft especially at the point of intended staple discharge. For example, a pressure of about 2 psi may be required to assure staple penetration through an endograft and a vessel wall such as an aortic wall. In other embodiments, however, there is no balloon 132 and once the expandable portions 126 are expanded, staples can be discharged without the need for balloon inflation. That is, the expandable portions 126 are expanded without the need for added pressure from a balloon where the enhanced pressure on the endograft and vessel is provided by locking the strut members in their expanded position. In one embodiment, the expandable portions 126 may be configured to provide a firm contact between the vessel and an endograft. In another embodiment, a stent or other expansion type structure can be used in conjunction with the expandable portions 126 to provide such firm contact.

Figure 6:
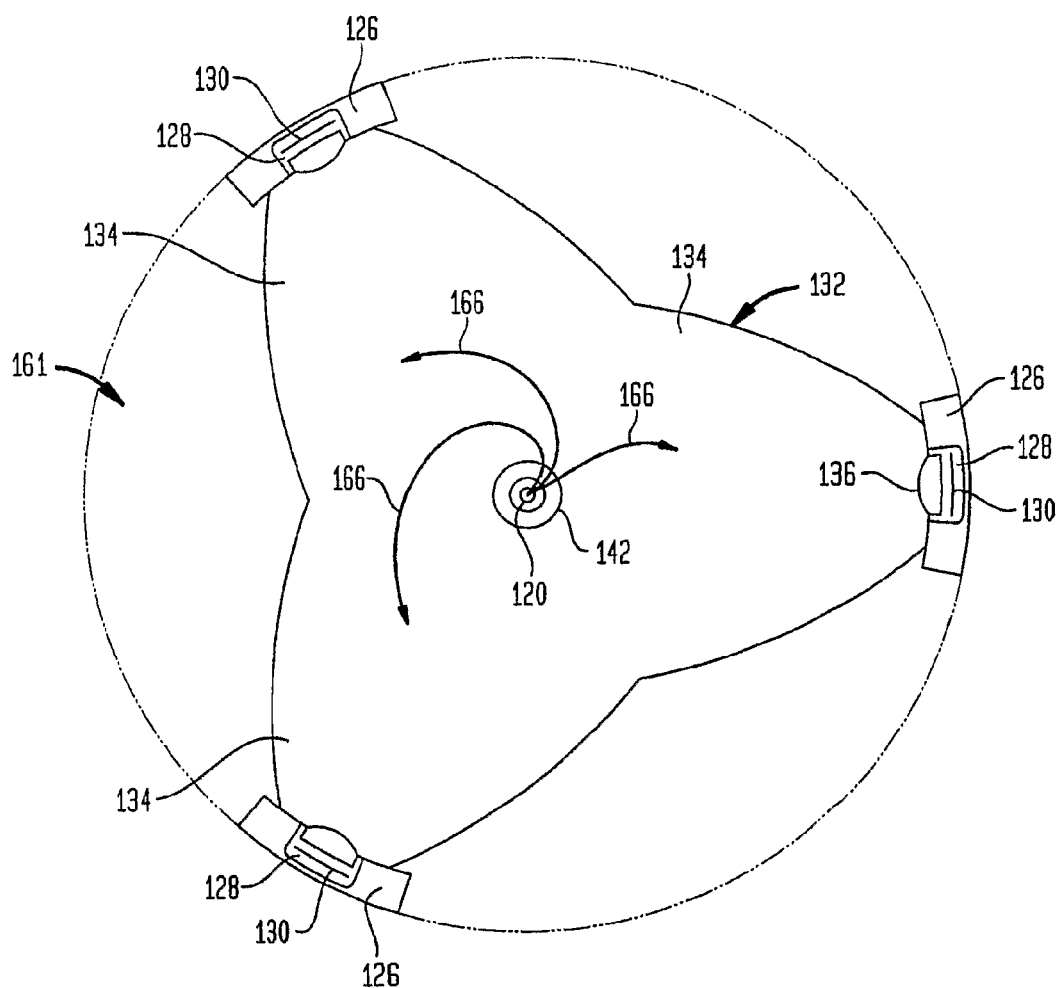
FIG. 6 is a cross-sectional view of the staple housing of FIG. 5 taken along section lines B-B showing the balloon segments being attached to the inner surface of a corresponding strut member.

FIG. 5 is a detailed view of the staple housing 104 of FIG. 4 showing balloon 132 inflated within the staple housing 104. FIG. 6 is a cross-sectional view of the staple housing of FIG. 5 taken along section lines B-B. FIGS. 5 and 6 show the balloon 132 in an inflated condition and FIG. 4 shows the balloon 132 in a partially deflated condition. In one embodiment, the balloon may be a partially compliant balloon to completely conform to the diameter of the aortic neck and generate the necessary pressure for staple penetration of the endograft and vessel wall. In one embodiment, the balloon 132 is adapted to complement the configuration of the expandable portions 126. For example, as explained above, the staple housing 104 comprises three evenly spaced expandable portions 126 with interior and exterior facing surfaces. Each expandable portion 126 comprises a staple cartridge 128 with an exit area 130 extending from the exterior surface of the portion through which staples can be discharged.

To complement the structure of the expandable portions 126, the balloon 132 can be star shaped (along a cross-section, see FIG. 5 or 6) with three evenly spaced wedge shaped segments 134. The segments 134 can be configured in such a manner where each segment is attached to the interior surface of a corresponding expandable portion 126. That is, each segment 134 is attached to a surface opposite the exit area 130 of a corresponding staple cartridge 128. The segments 134 can be attached to the expandable portions 126 using a biocompatible adhesive 136 or other well-known fastening techniques. In another embodiment, three separate balloons, either connected to the staple cartridges or not, may also be used. For example, a plurality of balloons or a single balloon may be configured to engage each of the expandable portions 126. In other embodiments, the balloon can be configured to engage a combination of the expandable portions 126 and an endograft. In one embodiment, even when deflated, the outer edges of the balloon segments are still attached to the inner surface of the corresponding expandable portion 126 (e.g., strut member) so that expansion of the expandable portions expands and unfolds the balloon.

In one embodiment, the balloon inflation channel 142 can be located central to the balloon 132 and concentric with the guide wire 120 and corresponding guide wire channel. The balloon channel 142 includes a single exit port 164 which allows for a flow of fluid, shown by arrow 166, into the interior of each segment 134 which helps inflate the balloon in an even manner. The segments are shown as being in fluid communication in FIG. 6. However, in other embodiments, the segments can be separate portions in fluid communication with separate balloon inflation channels.

The balloon 132 may be inflated prior to discharging staples (not shown) from the staple cartridges 128. One purpose of inflating the balloon 132 is to force the expandable portions 126 as well as the exit area 130 of the staple cartridges 128 against the area where the staple is to be discharged. This not only places the staple immediately adjacent to the receiving area, but it assists with preventing the staple cartridges 128 from being moved, linearly or rotationally due to the resistance presented by the endograft and vessel wall, during the firing of the staple.

Selective inflation and deflation of the balloon 132 is completed through the balloon inflation port 124 of the trigger housing 102 (FIG. 1). It will be appreciated that the balloon inflation port 124 may include a valve (not shown) upon which a liquid source (not shown) may be attached. The liquid source may be permitted to flow into the balloon inflation port 124 to inflate the balloon 132. Deflation of the balloon 132 may be accomplished at the balloon inflation port 124 by releasing liquid therefrom, such as by opening the valve or by sucking liquid out of the balloon 132 through use of the liquid source, which may have the capability of reversing direction of flow to form a vacuum. It will be appreciated that the balloon inflation port 124 is in fluid communication with the balloon 132 via the balloon inflation channel 142. Inflation and deflation may also be conducted with any of the available devices used for inflation and deflation of angioplasty balloons. Typically, the liquid used for inflating and deflating the balloon will be dilute contrast or saline.

The balloon 132 may provide non-occlusive features to help reduce occlusion of a vessel, such as the aorta, in which the staple housing is inserted. For example, the star shape of the balloon 132 pushes the expandable portions 126 outward and at the same time provides for large unobstructed areas 161 for unimpeded blood flow. The balloon 132 helps provide the required displacement of the staple cartridge with respect to the endograft and vessel wall without completely occluding the vessel lumen. Occlusion of a vessel, may be detrimental and is preferably avoided. In particular, interruption of blood flow during each staple deployment cycle, though brief, may detract from an advantage of stapling using endovascular techniques; namely, the absence of aortic cross-clamping. Further, complete occlusion may result in instability of the stapling mechanism due to the pounding inflicted on the balloon by the attempted blood flow. In severe cases, the pounding may result in caudad displacement of the endograft. The detrimental physiologic effects of complete occlusion may be typically more pronounced in the thoracic region, but may occur elsewhere as well. The balloon 132 of the present application may help reduce occlusion while providing proper positioning of the staple cartridge to the endograft and the vessel wall.

FIG. 7 is a perspective view of the staple housing of FIG. 5 showing the discharge of staples 180. The staple housing 104 is shown with the expandable portions 126 in an expanded position and with the balloon 132 (shown in dashed line for clarity) in an inflated condition. To discharge the staples 180, the actuator wire 150 is urged in a direction, shown by arrow 153, opposite the distal end 110, where such movement causes the staples 180 from each of the staple cartridges 128 to be discharged substantially simultaneously. In one embodiment, the first trigger 116 located at trigger housing 102 (FIG. 1) can be used to actuate the discharge of the staples. For example, the first trigger 116 can be rotated a predetermined amount, such as a ¼ turn, which causes the wire 150 to move in the above manner and staples to be discharged from the staple cartridges. In other embodiments, other devices well known in the art can be used to convert such rotational movement into linear movement. In addition, the indicator 122 (FIG. 1) is updated to provide an indication of the number of staples discharged. In the above manner, three equally spaced staples 180 are discharged in a substantially simultaneous manner and used to secure an endograft to a vessel. In another embodiment, the staples can be discharged in sequential manner with one staple being fired from one staple cartridge and then another until all of the staples have been discharged from all of the staple cartridges. In one embodiment, more than three staples can be used to further improve the attachment between the endograft and the vessel. The staple cartridges 128 can be configured to hold one or more staples in tandem such that when one staple is discharged from the staple cartridges another staple is automatically moved into place and ready to be discharged through the same staple cartridge through a subsequent discharge application or cycle. The staple housing 104 is configured to discharge three staples during a single application to pierce and secure an endograft to vessel.

The staple housing 104 is capable of being activated again to discharge a second set of multiple staples. It may be desirable to provide additional staples for a more secure attachment between the endograft and the vessel. For example a total of six staples can be discharged; three from a first discharge application and another three from a second discharge application following rotation of the stapler. The six staples can be equally spaced apart or clustered depending on particular requirements. This can be accomplished by using the staple housing to apply an additional set of three staples during a second discharge application. In particular, in operation, the balloon 132 is deflated and then the staple housing 104 is rotated to another position such that staple cartridges are located between the staples previously discharged during the first application. The balloon 132 can now be re-inflated and the staple cartridges can be actuated to discharge a second set of staples to pierce and hold the endograft to the vessel in a more secure manner. In other embodiments, the staple housing can be configured to discharge a different number of staples by providing a staple housing with a different number of expandable portions and corresponding staple cartridges to meet different application, performance and manufacturing requirements. For example, the staple housing 104 can be configured to have 2, 4, 5, 6, 7 or 8 expandable portions and corresponding staple cartridges the only requirement being that the staple be capable of being accommodated within the space provided by each expandable portion.

Figure 8A:
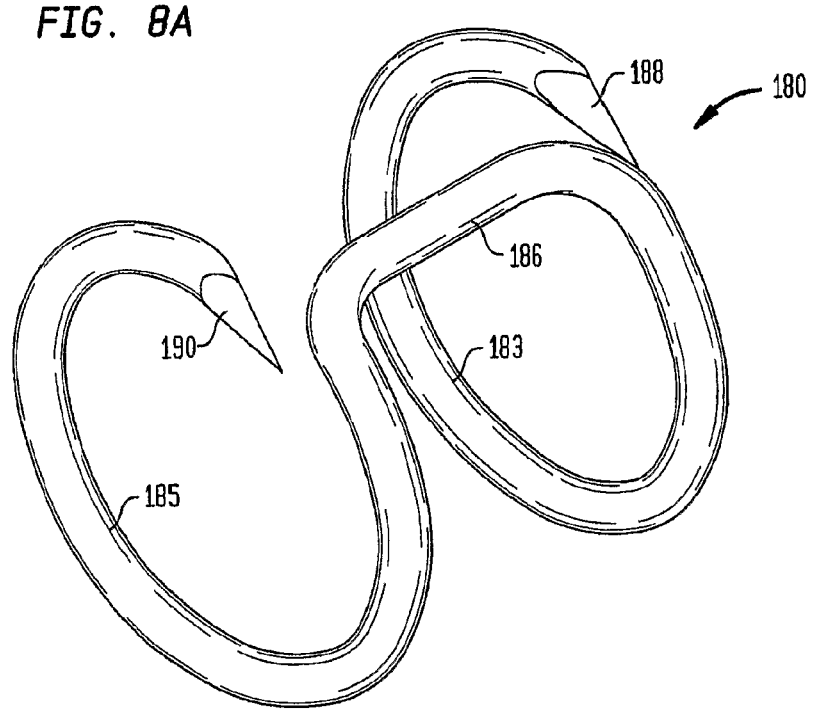
FIG. 8a is a detailed perspective view of the staple form of FIG. 7 which it is designed to assume following complete discharge from a staple cartridge.
Figure 8B:
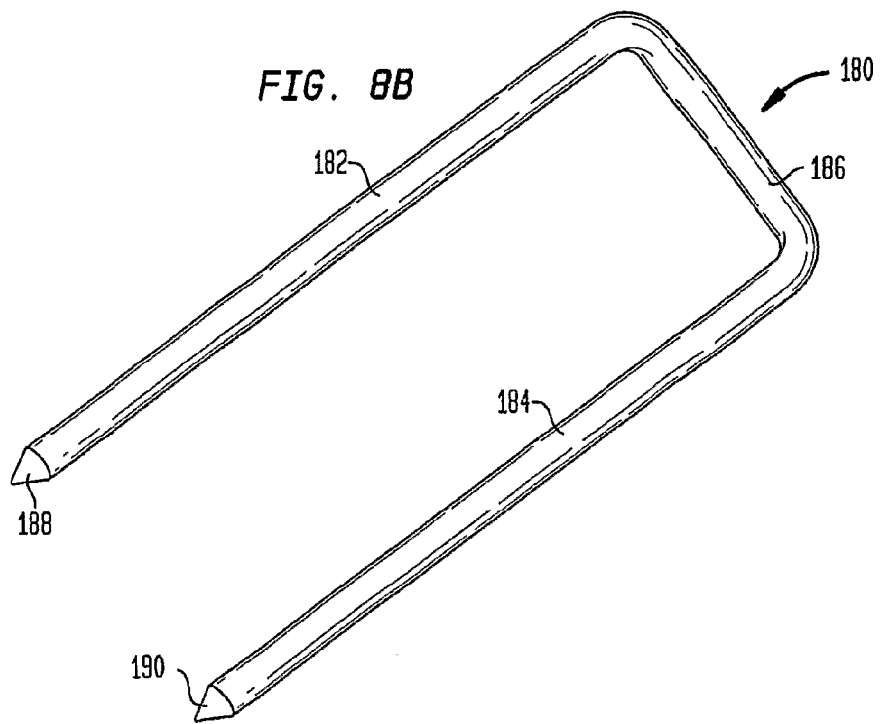
FIG. 8b is a perspective view of the staple shown in FIG. 8a in its stretched condition in which it is loaded within a staple cartridge prior to the beginning of the discharge process.

FIG. 8a provides a detailed view of the staple 180 which may be utilized with the staple cartridge 128 of the present application as shown in FIG. 7. FIG. 8a shows the staple 180 in its natural condition. Preferably, the staple 180 is constructed of a memory alloy such as Nitinol, as is commonly used in the art. Within the staple cartridge 128 (FIG. 7), the staple 180 will typically be deformed into the condition shown in FIG. 8b. As shown in FIG. 8b, the staple 180 may be predominantly U-shaped in its deformed condition and may comprise a pair of legs 182, 184 connected by a central portion 186. Each of the pair of legs 182, 184 may terminate with spiked ends 188, 190 which aids the penetration of the endograft and vessel.

Upon application into the endograft and vessel utilizing the techniques to be discussed, the staple 180 may be permitted to return back to its natural condition into the shape shown in FIG. 8a. As shown, the legs 182, 184 may be bent into loops 183, 185 such that the spiked ends 188, 190 are adjacent to the central portion 186. During the application process, the spiked ends 188, 190 may pierce the endograft and vessel so as to securely attach the two together.

Figure 9:
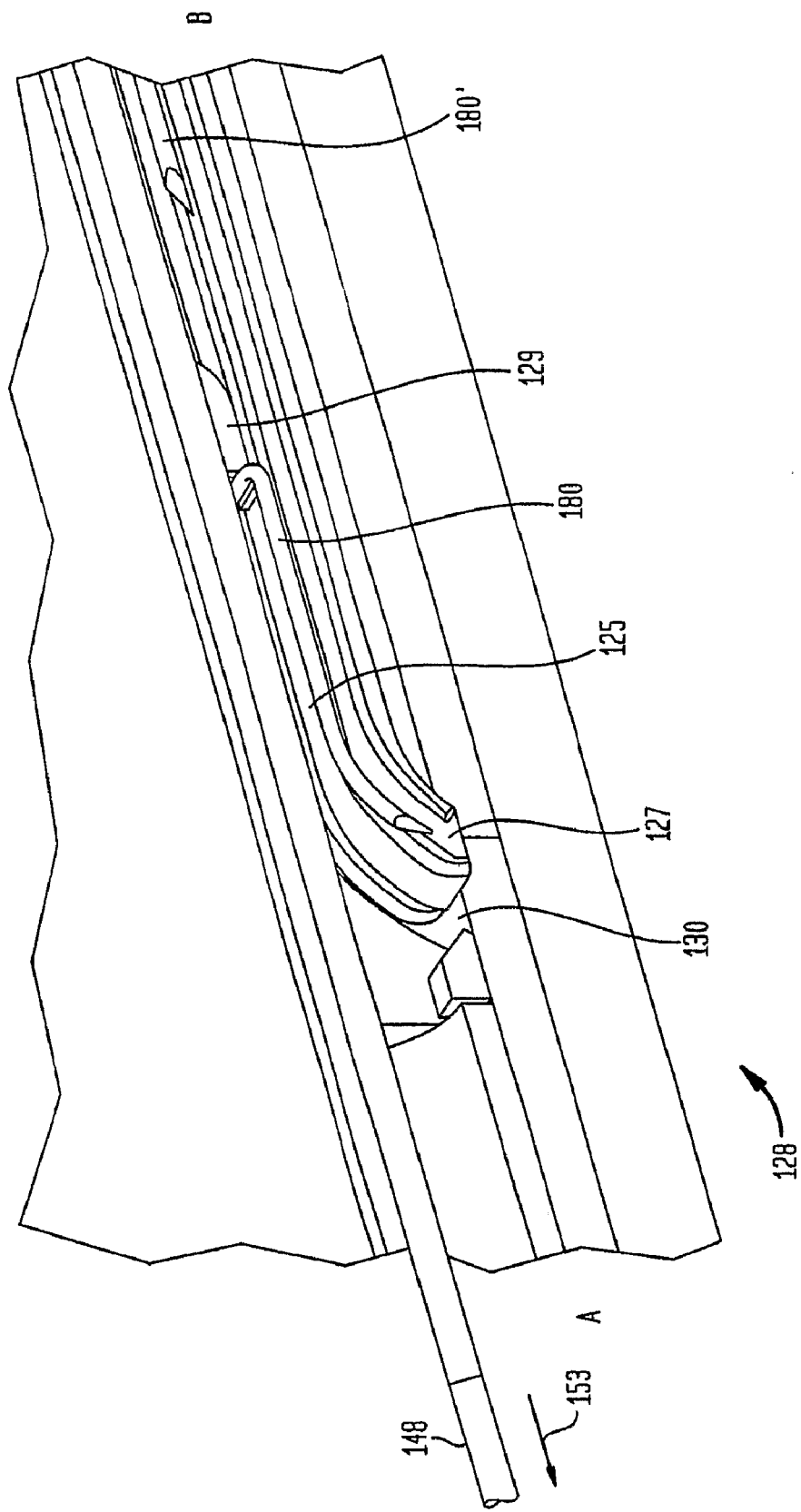
FIG. 9 is a longitudinal sectional view of the staple cartridge of FIG. 4 taken along section lines C-C.

FIG. 9 is a longitudinal sectional view of the staple cartridge of FIG. 4 taken along section lines C-C. A plurality of staples 180, 180' may be pre-placed in tandem within the staple cartridge 128, prior to entry into the patient. The staples 180, 180' can be stretched from their natural condition (FIG. 8a) prior to loading within the staple cartridge 128. The actuator wire 148 has one end connected to a staple pusher element 129 of the staple cartridge 128 and another end connected to the trigger 116 of the trigger housing 102 (FIG. 1). In one embodiment, the trigger 116 may be used to pull the staple pusher 129 in a direction shown by arrow 153 toward the trigger housing. As the staple 180 is pulled, in the direction shown by arrow 153, by the staple pusher 129 in conjunction with the trigger, the staple 180 may travel along the arcuate path of the internal staple guide 125 bounded partially by flanges (conformator) 127 and the limits of the internal staple guide. As explained below in further detail, as the wire is advanced further in the direction by arrow 153, the staple 180 is pushed and discharged from the exit area 130. Upon discharge, the staple 180 may be permitted to return back to its natural condition (FIG. 8a) such a return being delayed by the conformator 127 until it has pierced the endograft and vessel so as to securely attach the two together. As will be discussed, the staples may also be pushed in position toward the distal end of the stapler rather than pulled toward the proximal end.

Referring to FIG. 1, generally, advancement of the endovascular stapler 100 is considered to be via an "over the wire" type system. As an "over the wire" device, the staple housing 104 portion of the stapler 100 is designed to be guided through vessels following the path of a previously installed guide wire 120. For example, a guide wire 120 may be placed in an artery in a surgical procedure. The distal end 110 of the staple housing 104 may then be pushed along the length of the guide wire 120, which travels from a guide wire exit point at the distal end 110, through the guide wire channel 140 and out the port 119 of the trigger housing 102. Once the distal end 110 reaches its destination, advancement may cease and the stapler 100 is ready to discharge a plurality of staples simultaneously during a single application. It will be appreciated that the staple housing 104 may be constructed of flexible materials such that it may bend as necessary along the path toward the area in which the staples are to be discharged or that a stiff guide wire may be used to "straighten the path", a technique frequently used in the practice. It may also be desirable to follow an external guide wire or rail or not to have a guide wire at all.

Preferably, the endovascular stapler of the present invention is designed to fit through a 16 French sheath for aortic and iliac arterial use. However, it is also foreseeable that the stapler may be miniaturized to fit through smaller sheaths for fixation of endografts in smaller caliber vessels.

Figure 10:
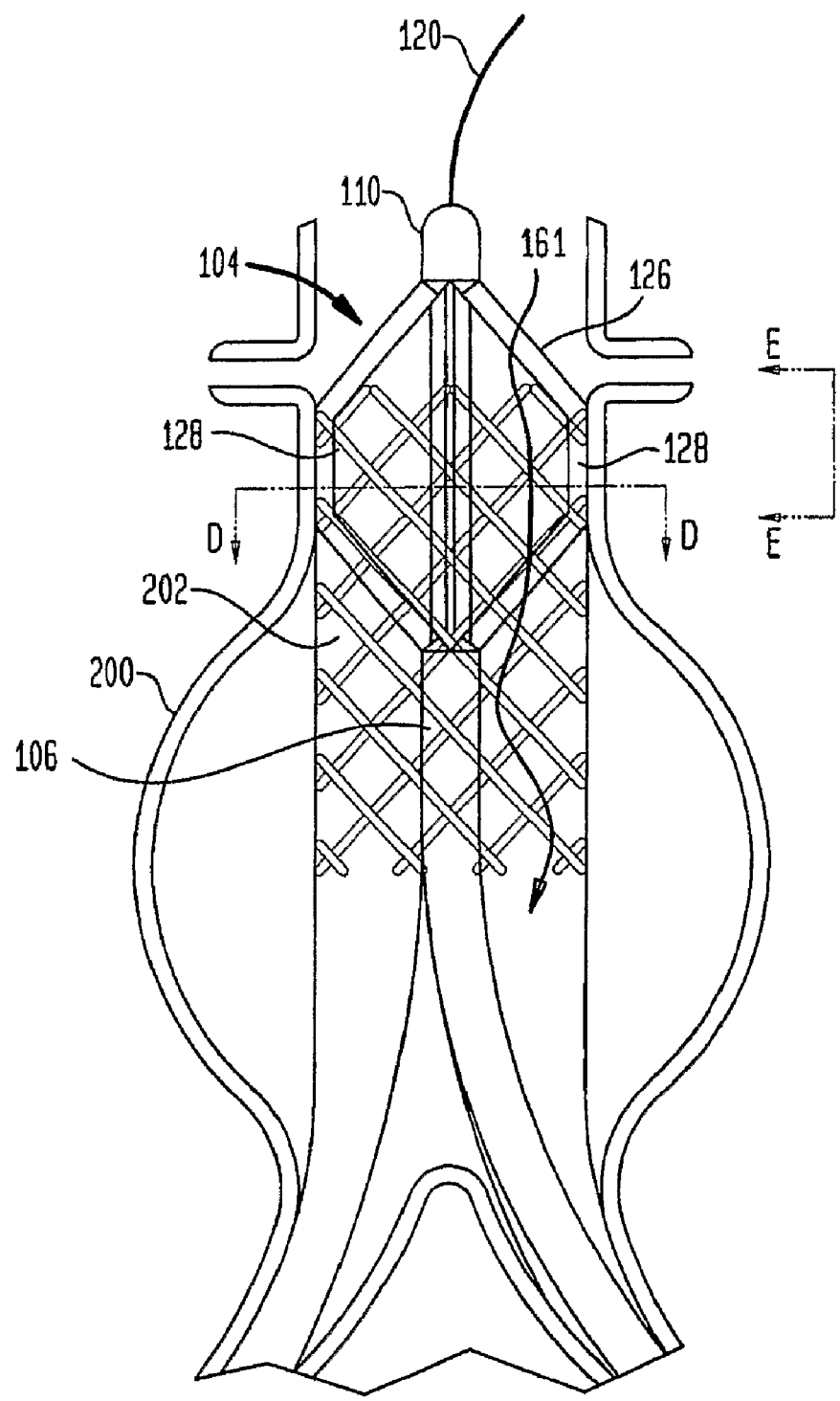
FIG. 10 is a depiction of a frontal sectional view of the abdominal aorta showing the general orientation of the stapler with the strut members forming a cage structure utilized in a method of securing an endograft to the aorta in accordance with one embodiment of the present invention.

FIG. 10 depicts a staple housing 104 inserted into a sheath within the human body. In one embodiment, staple housing 104 is inserted into a vessel 200 such as the aorta. The staple housing 104 is typically introduced into the femoral artery in the groin or other suitable access area where it follows the previously inserted guide wire 120 into the lumen of an endograft 202 to be stapled. As explained below in detail, the staple housing 104 has a plurality of expandable portions 126 each having a staple cartridge 128 for discharging staples to secure endograft 202 to the vessel 200. In this manner, a plurality of staples can be discharged simultaneously during a single discharge application. The staple housing 104 also permits fluid flow, shown by arrow 161, in a non-occlusive manner as explained further below.

Figure 11:
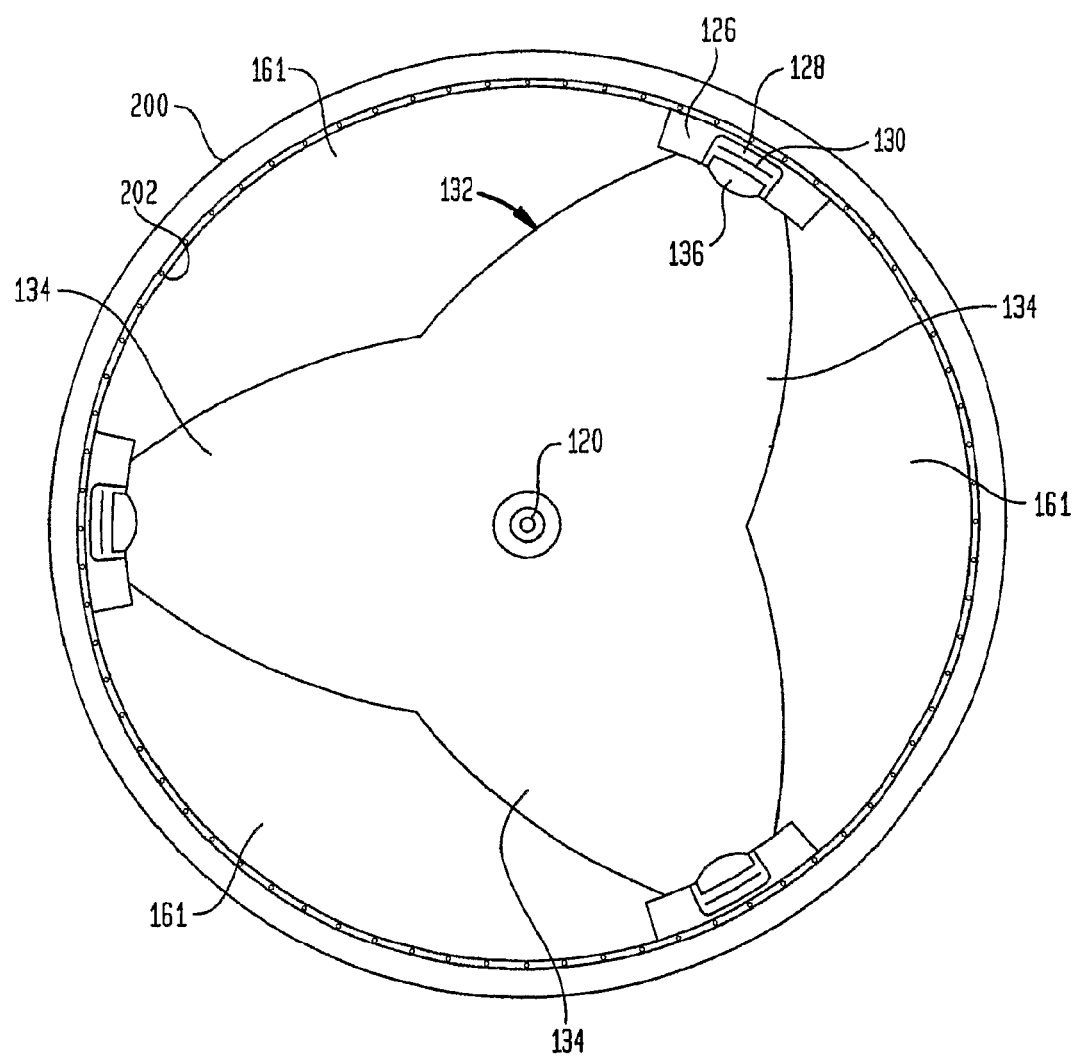
FIG. 11 is a cross-sectional view of the abdominal aorta, endograft, stapler strut members, and star shaped non-occlusive balloon of FIG. 10 taken along section lines D-D.

FIG. 11 is a cross-sectional view of the staple housing of FIG. 10 taken along section lines D-D. The staple housing 104 is disposed in a first position against the endograft and the vessel to discharge a first set of staples during a discharge application or cycle. The expandable portions 126 are shown in the expanded position. Also, the balloon 132 is in a fully inflated condition. As previously explained, the balloon 132 provides non-occlusive features because it helps reduce occlusion of the vessel in which the staple housing is inserted. As shown, the balloon 132 pushes the expandable portions 126 outward and at the same time provides for large unobstructed areas 161 for blood flow.

As previously discussed, the staple cartridges 128 of the staple housing 104 will be pushed against the endograft 202 and vessel sidewall 200 by the expandable portions 126 and further pushed by the inflated balloon 132. When so pushed, the plurality of staple cartridges 128 can be actuated to discharge a first set of staples therefrom so to secure the endograft 202 to the vessel 200. In one embodiment, the first set of staples includes three staples discharged from the staple cartridges 128. The staple housing 104 can be configured to discharge a second set of staples to help improve the attachment between the endograft 202 and the vessel 200. This can be accomplished by deflating the balloon 132 and rotating the staple housing 104 around the longitudinal axis of the stapler to a second position. In one embodiment, the staple housing can be positioned in such a manner to discharge the second set of staples between previously discharged first set of staples. Next, the balloon 132 is then re-inflated such that the staple cartridge 128 is aligned at the intended deployment location and the staple cartridges 128 are actuated so to discharge the second set of staples to the desired location. In this manner, a total of six staples can be discharged so to improve the attachment between the endograft 202 and the vessel 200. In other embodiments, the staple housing 104 can be configured to store additional staples so to discharge a third set of staples. The process of discharging staples from the staple cartridge 128 is described below in detail.

Figure 12:
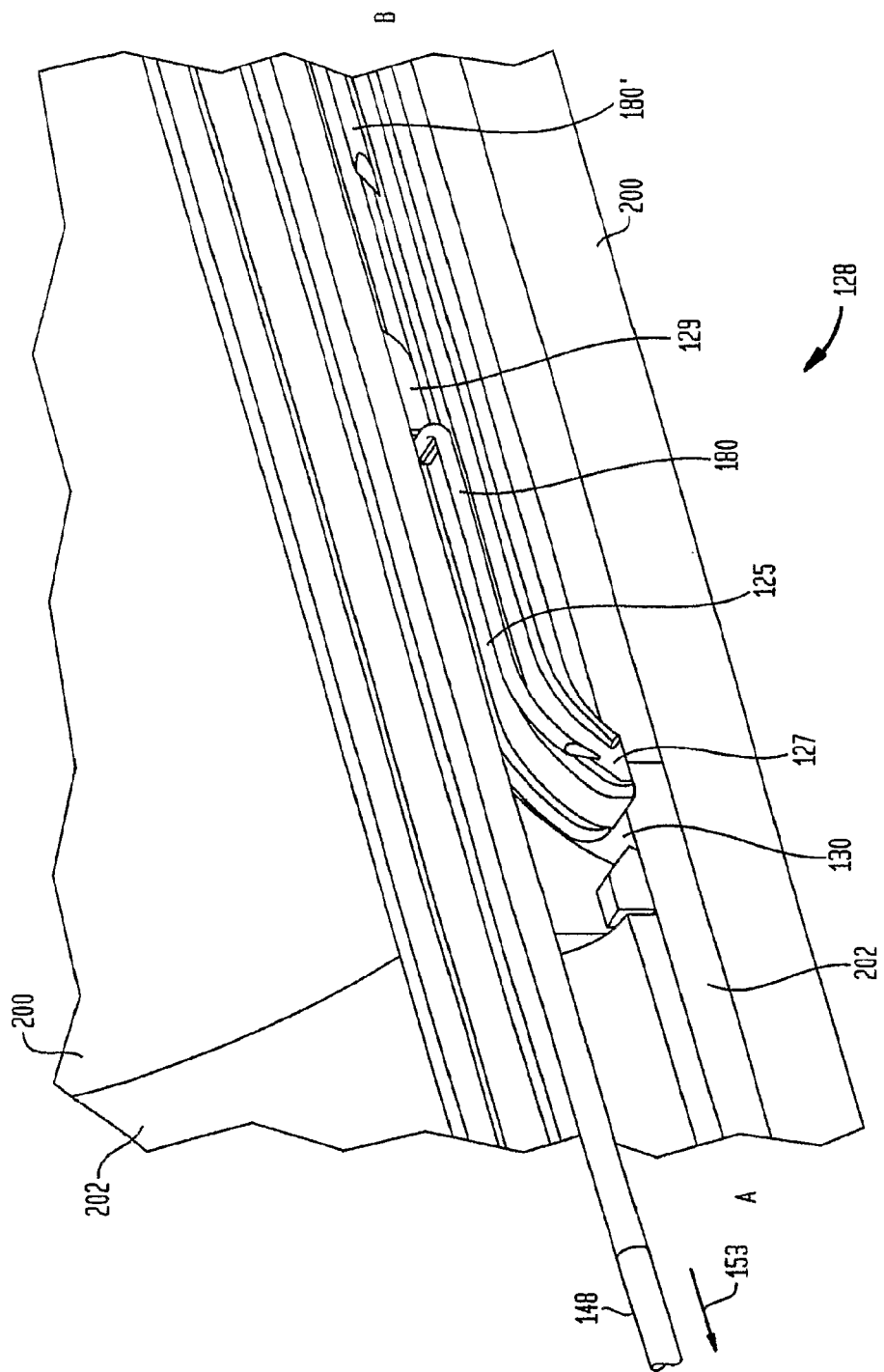
FIG. 12 depicts a cut-away view of the staple cartridge of FIG. 10 discharging a staple during an initial step of process in accordance with one embodiment of the present application.

FIG. 12 is a longitudinal sectional view of the staple cartridge of FIG. 10 taken along section lines E-E. In preparation for discharging staples, a plurality of staples 180, 180' may be pre-placed in tandem within the staple cartridge 128. The actuator wire 148 is pulled in the shown by arrow 149 which causes the staple pusher 129 to move in the same direction. As a result of such movement, staple 180 travels along the arcuate path of the internal staple guide 125 bounded partially by flanges 127 and the limits of the internal staple guide. The wire is advanced further in the direction by arrow 153 to cause the staple to discharge as explained below in detail. The surface of the conformator 127 may be coated with a metal and is therefore radiopaque. This may help make placement of the staples extremely accurate as the staple exit site can be clearly seen on standard fluoroscopy.

Figure 13:
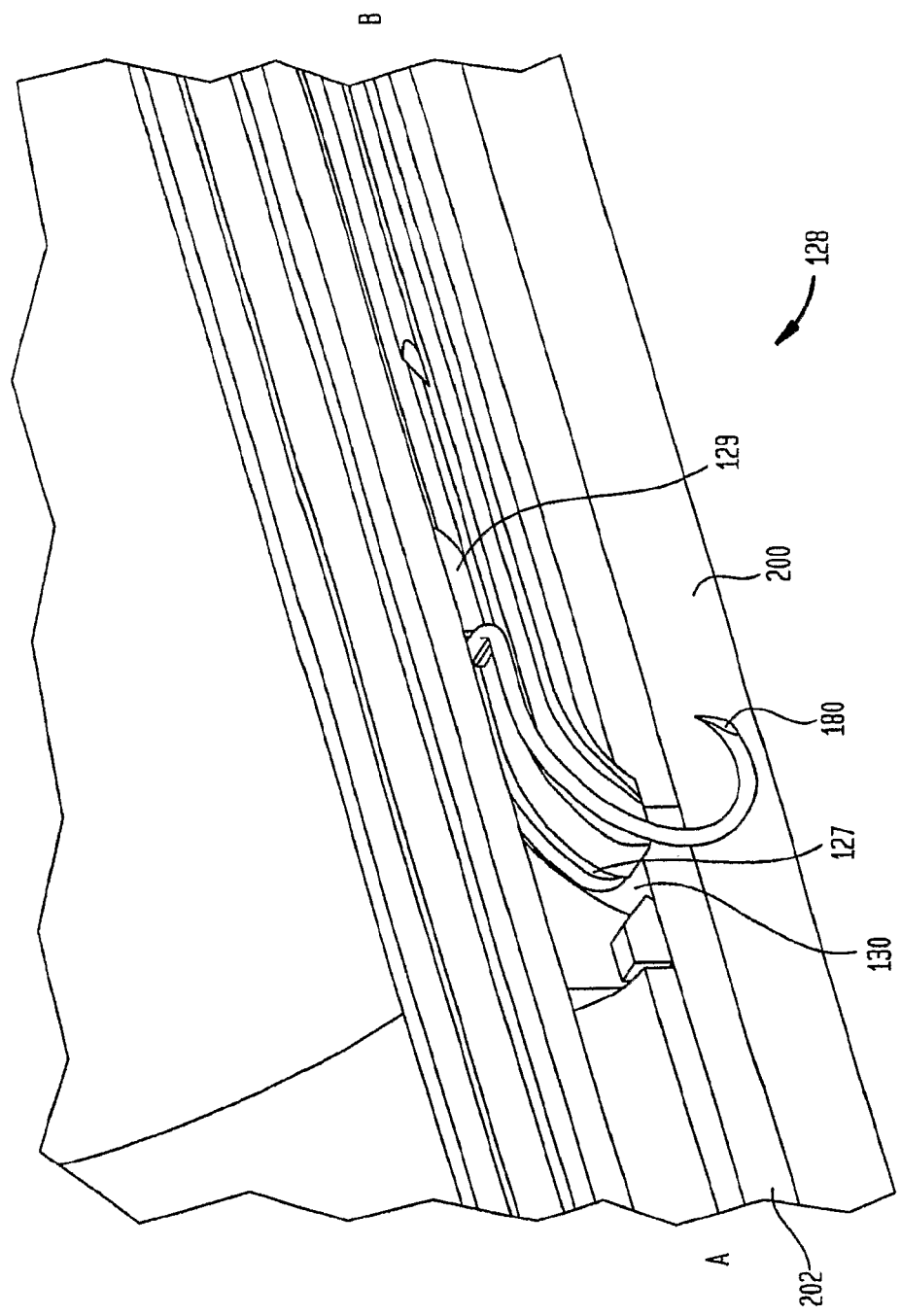
FIG. 13 depicts a cut-away view of the staple cartridge of FIG. 10 during a further step of discharging a staple.

FIG. 13 depicts a further step in this process. As shown in FIG. 13, as the staple travels further, the straight legs 182, 184 of the staple 180 may be permitted to form back into loops 183, 185 as the staple is pushed forward toward the staple exit area 130. The leading spiked ends 188, 190 may therefore penetrate the endograft 202 and the vessel wall 200 as the loops 183, 185 are formed. Formation of such loops 183, 185 preferably secures the endograft 202 to the vessel wall 200. As with previous embodiments, it will be appreciated that a non-compliant balloon or other device may be utilized to ensure that the staple exit area 130 is directly adjacent to the endograft 202 to be stapled, and that the endograft is pressed against the vessel wall 200.

Sizing of the loops 183, 185 may be advantageously controlled by selection of an appropriate staple 180. Accordingly, a staple 180 with a given loop diameter in its natural condition should return to that loop diameter upon discharge from the staple exit area 180, regardless of the geometry of the internal staple guide 125. In this regard, several sized staples may be utilized with a single endovascular stapler. Typically, staple loops 183, 185 range in size from approximately 2 mm to 6 mm, with 3 mm or 4 mm being a common size for fixation with the aorta. For smaller or thinner vessels, 2 mm preformed loops are typical. Under normal conditions, the diameter or caliber of the various staples 180 remains constant though their loops 183, 185 may vary in diameter. If required, the diameter or caliber of the staple 185 may also be varied.

Figure 14:
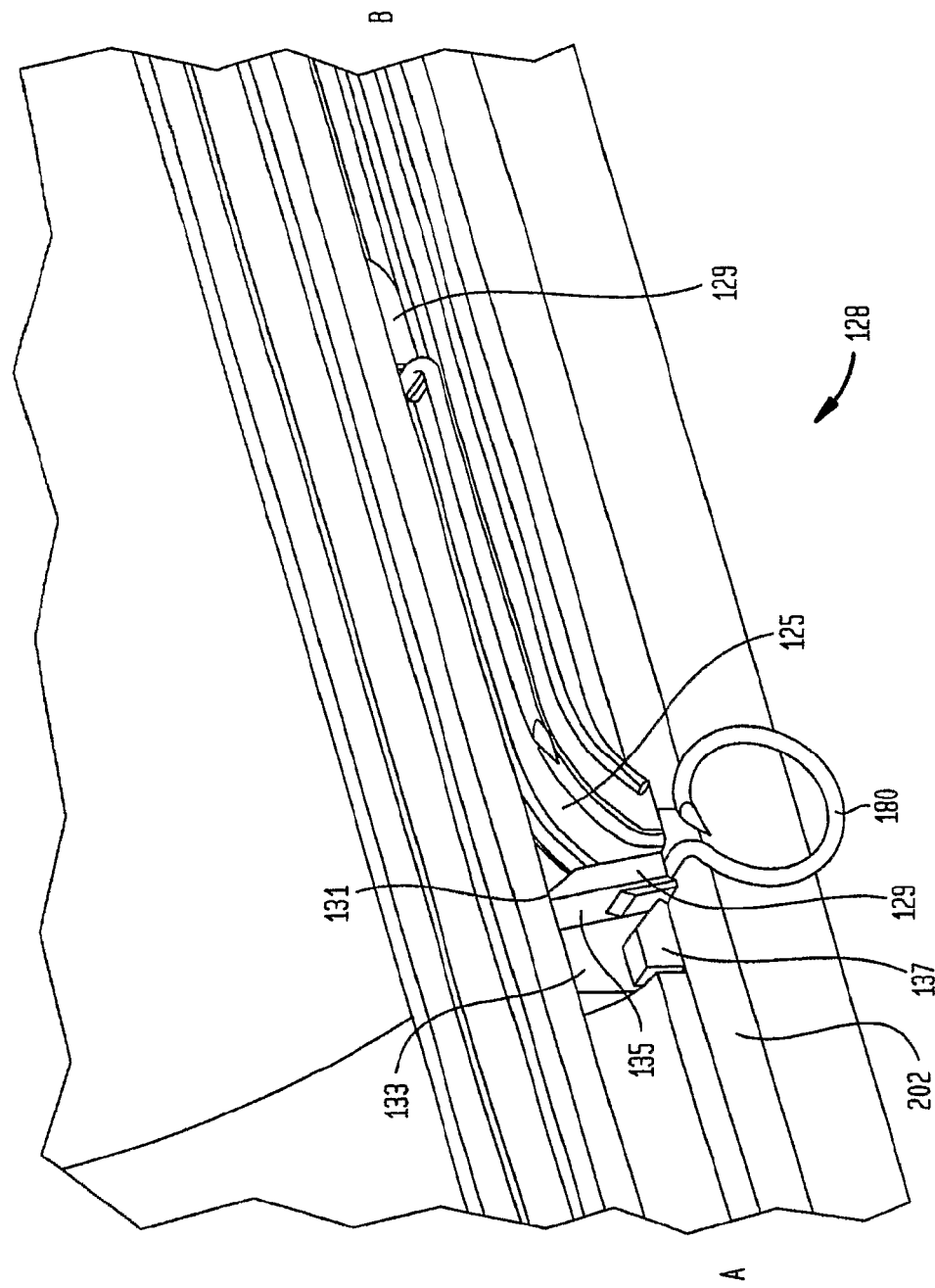
FIG. 14 depicts a cut-away view of the staple cartridge of FIG. 10 during a still further step of discharging a staple.

A further step in the method of deploying staple 180 is shown in FIG. 14. As shown in FIG. 14, the staple pusher 129 may be permitted to pivot about its heel 131 into the open space 133 provided in the internal staple guide 125 near the staple exit area 130 such that it preferably pushes the central portion 186 of the staple 180 completely against the endograft 202 while the loops 183, 185 are formed. The natural action of the staple 180 in forming the loops 183, 185 may also assist with securing the staple in place. The length of the pivoting portion 135 of the staple pusher 129 may be strategically designed to approximately equal the height of the internal staple guide 125 such that upon rotation of approximately 90 degrees, the rotating portion 135 of the staple pusher will fill the height of the internal staple guide to push the central portion 186 of the staple completely against the endograft 202.

Upon initiation of rotation of the rotating portion 135 of the staple pusher 129, the rotation portion may contact a fixed block 137 provided for that purpose. The fixed block 137 serves to further rotate the rotating portion 135 of the staple pusher 129 to angles beyond 90 degrees, such as is shown in FIG. 15 depicting a still further step in the method of deploying staple 180.

Figure 15:
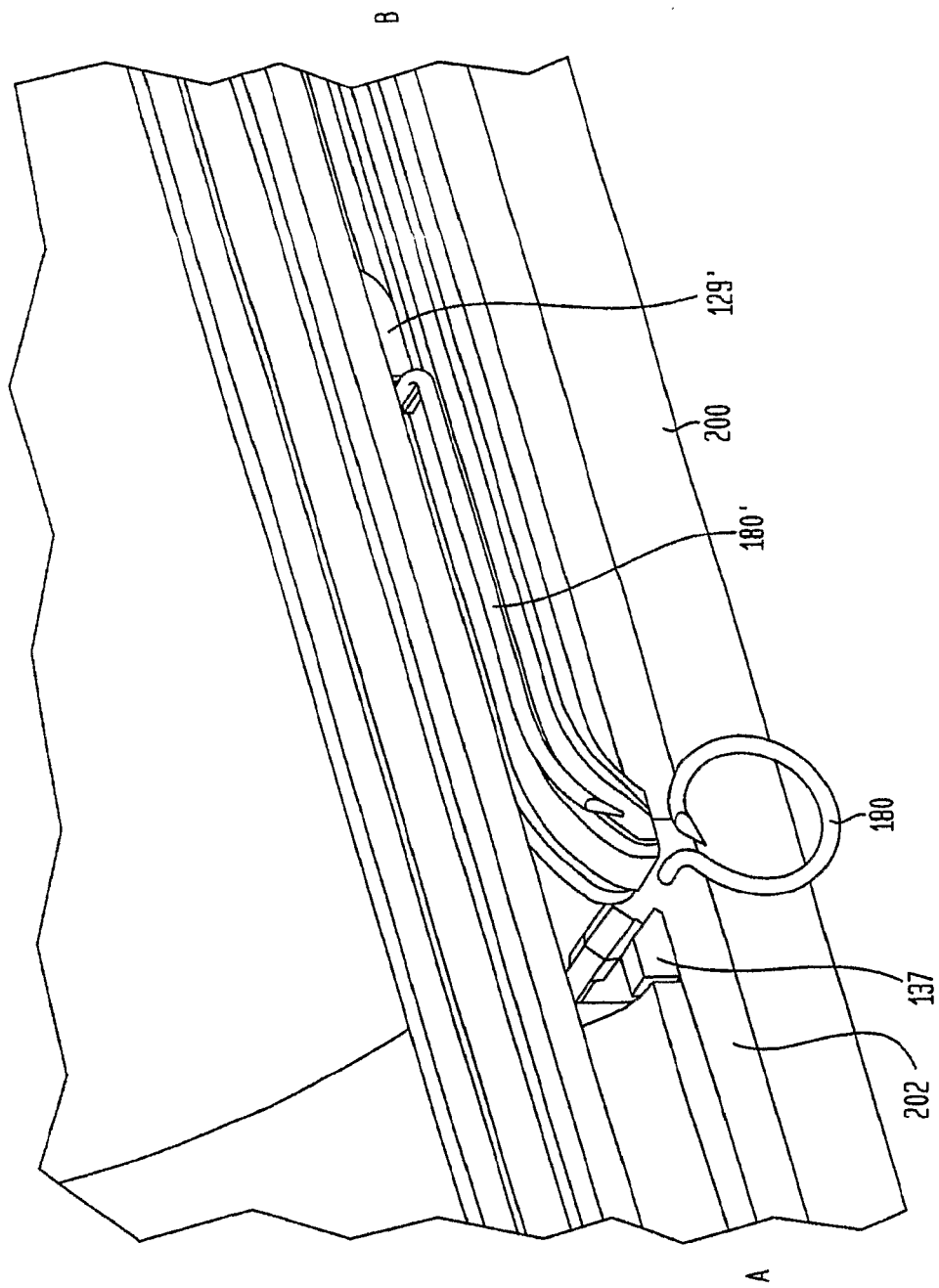
FIG. 15 depicts a cut-away view of the staple cartridge of FIG. 10 during a still further step of discharging a staple.

As the rotating portion 135 of the staple pusher 129 is further rotated and positioned away from the staple exit area 130, a second staple 180' may be brought toward the staple exit area by a second staple pusher 129' as shown in FIG. 15. The partially compliant balloon or similar device may then be manipulated to permit rotation of the staple housing 104 such that the staple exit area 130 is rotated or otherwise moved to a position adjacent to the previously deployed staple 180. The partially compliant balloon or similar device may then be manipulated to push the staple exit area 130 against the endograft 202 and the endograft against the vessel wall 200 in preparation of the firing of the second staple 180'.

A partially cut-away view of staple 180 completely installed into an endograft 202 and a vessel wall 200 is shown in FIG. 16. It will be appreciated that a series of staples 180 installed side by side may be utilized to completely attach the endograft 202 to the vessel wall 200, around the circumference of the endograft. Typically, a series of six to eight staples 180 may be utilized. As such, a single staple housing may house six to eight staples so the device need only be inserted into the patient once, while still being capable of driving the requisite number of staples 180.

Referring back to FIG. 14, it will be appreciated that the staple 180 is depicted as being driven away from the patient's heart, the heart being toward the direction labeled B in the figure. In other embodiments, the identical staple 180 may be driven toward the heart. In such case, the trigger will serve to push the staple pusher 129, rather than pull the staple pusher. Installation of the endovascular driver is typically conducted in a direction toward the heart, regardless of the direction in which the staple 180 is driven.

Figure 17A:
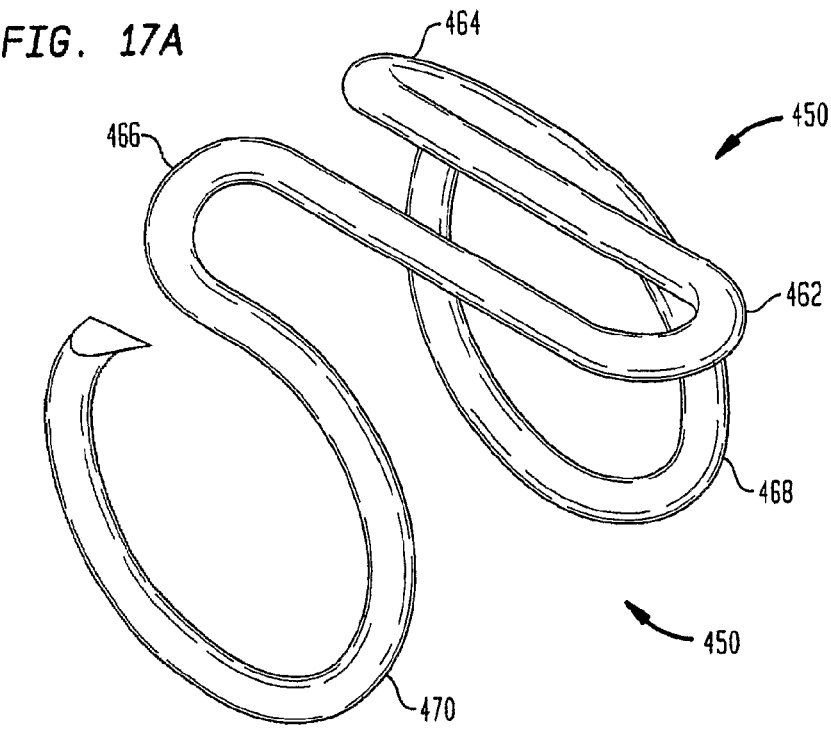
FIG. 17a depicts a perspective view of a staple type capable of being utilized with an endovascular stapler in accordance with a still further embodiment of the present application.

FIG. 17a depicts a staple 450 which may be utilized in conjunction with an endovascular stapler in accordance with a still further embodiment of the present invention. The condition shown in FIG. 17a is the staple's 450 natural condition. Preferably, the staple 450 is constructed of a memory alloy such as Nitinol, as is commonly used in the art. Within the staple housing of an endovascular stapler, the staple 450 will typically be deformed into the condition shown in FIG. 17b.

Figure 17B:
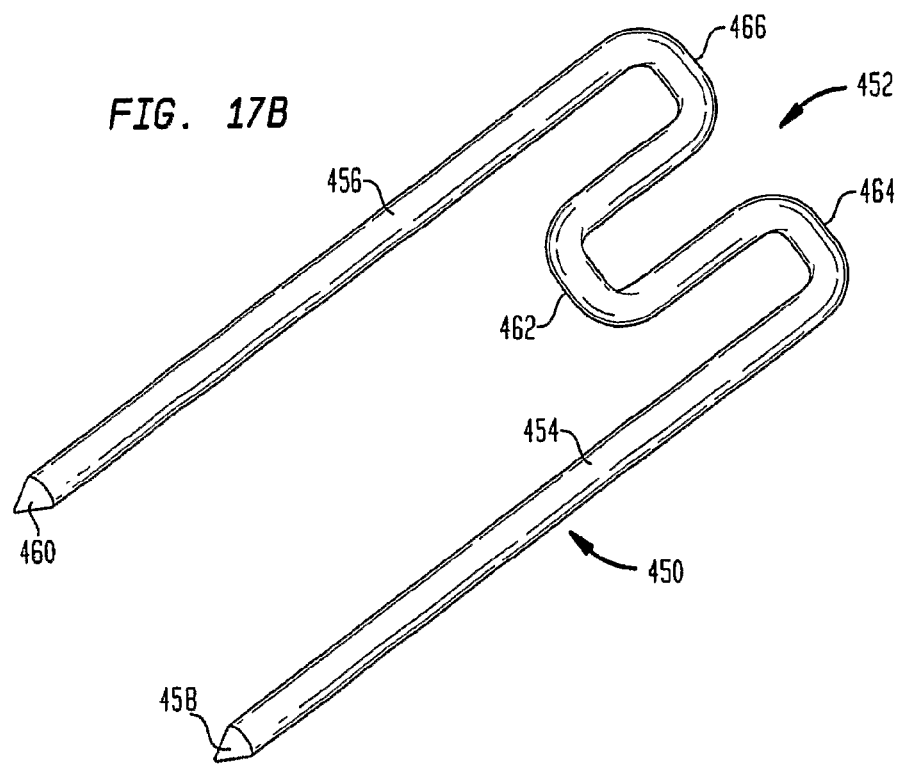
FIG. 17b depicts a perspective view of the staple shown in FIG. 17a in its stretched condition.

As shown in FIG. 17b, the staple 456 may be deformed to be predominantly U-shaped with a tongue area 452 between two legs 454, 456. Each of the pair of legs 454, 456 preferably terminates with spiked ends 458, 460.

The tongue area 452 of staple 450 generally comprises an inner U-shaped tongue 462 formed between two outer U-shaped curves 464, 466 partially forming the legs 454, 456, as depicted in FIG. 17b.

As shown in FIG. 17a, in the staple's 450 natural condition, the staple legs 454, 456 form loops 468, 470, the loops being bound between the spiked ends 458, 460 and the outer U-shaped curves 464, 466. As will be discussed, the tongue 462 may be biased by the outer U-shaped curves 464, 466 to apply pressure to tissue and other material held between the tongue and the loops 468, 470.

Figure 18:
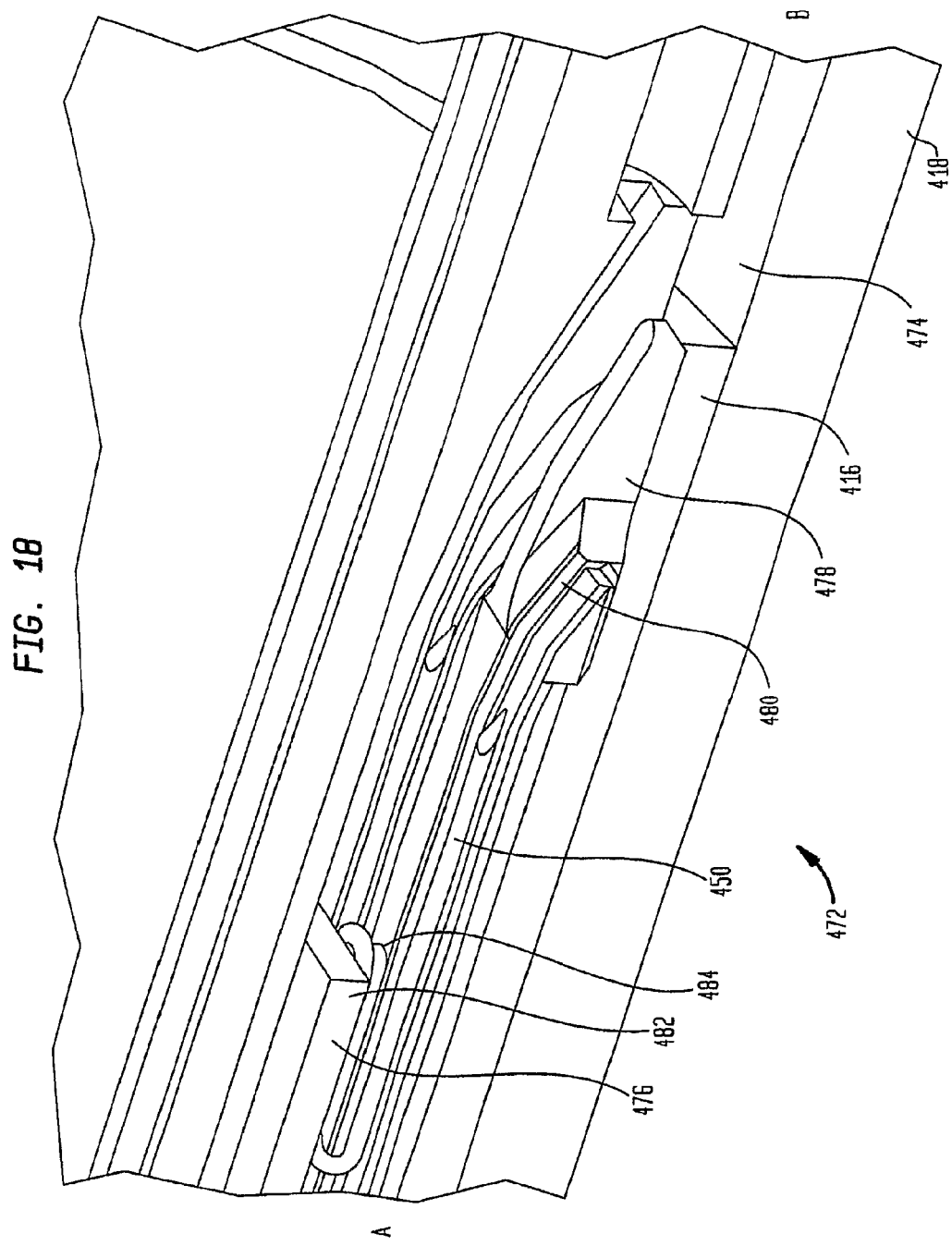
FIG. 18 depicts a cut-away view of a staple cartridge firing the staple of FIG. 17a during an initial step of one embodiment of the present application.

FIG. 18 depicts a cut-away view of the distal end of another embodiment of a staple cartridge 472 which may be utilized to deploy the staple 450 shown in FIG. 17b. The staple cartridge 472 can be used with the staple housing of the present application. It will be appreciated that the orientation of the staple cartridge 472 positioned in FIG. 18 is such that the patient's heart is located toward the side labeled B while an artery is located toward the side labeled A. The staple cartridge 472 is preferably inserted into the body from the side labeled A, toward the direction of the heart. In addition, it will be appreciated that the staples 450 are fired in a direction toward the heart, although they may also be fired in the opposite direction in other embodiments.

As shown in FIG. 18, the staple cartridge 472 may be placed such that the staple exit area 474 is adjacent to an endograft 416 intended to be connected to a vessel wall 418. As discussed with respect to other embodiments of the present invention, a non-compliant balloon or other structure may be utilized to maintain this position.

Staples 450 may be pre-placed in tandem within the staple cartridge 472, prior to entry into the patient. The trigger of the stapler can push the staple pusher 476 away from the stapler body to fire the staple 450 through the staple exit area 474. As the staple 450 is pushed away from the stapler body by the staple pusher 476 in conjunction with the ratcheting trigger, the staple 450 may travel along the arcuate path of the internal staple guide 478 bounded partially by flanges 480 and the limits of the internal staple guide.

The staple pusher 476 in this embodiment preferably comprises an upper plate 482 and a lower extension member 484 extending downward therefrom. As shown in FIG. 18, the lower extension member is preferably sized and configured to fit within the tongue 462 of the staple 450, between the U-shaped curves 464, 466.

Figure 19:
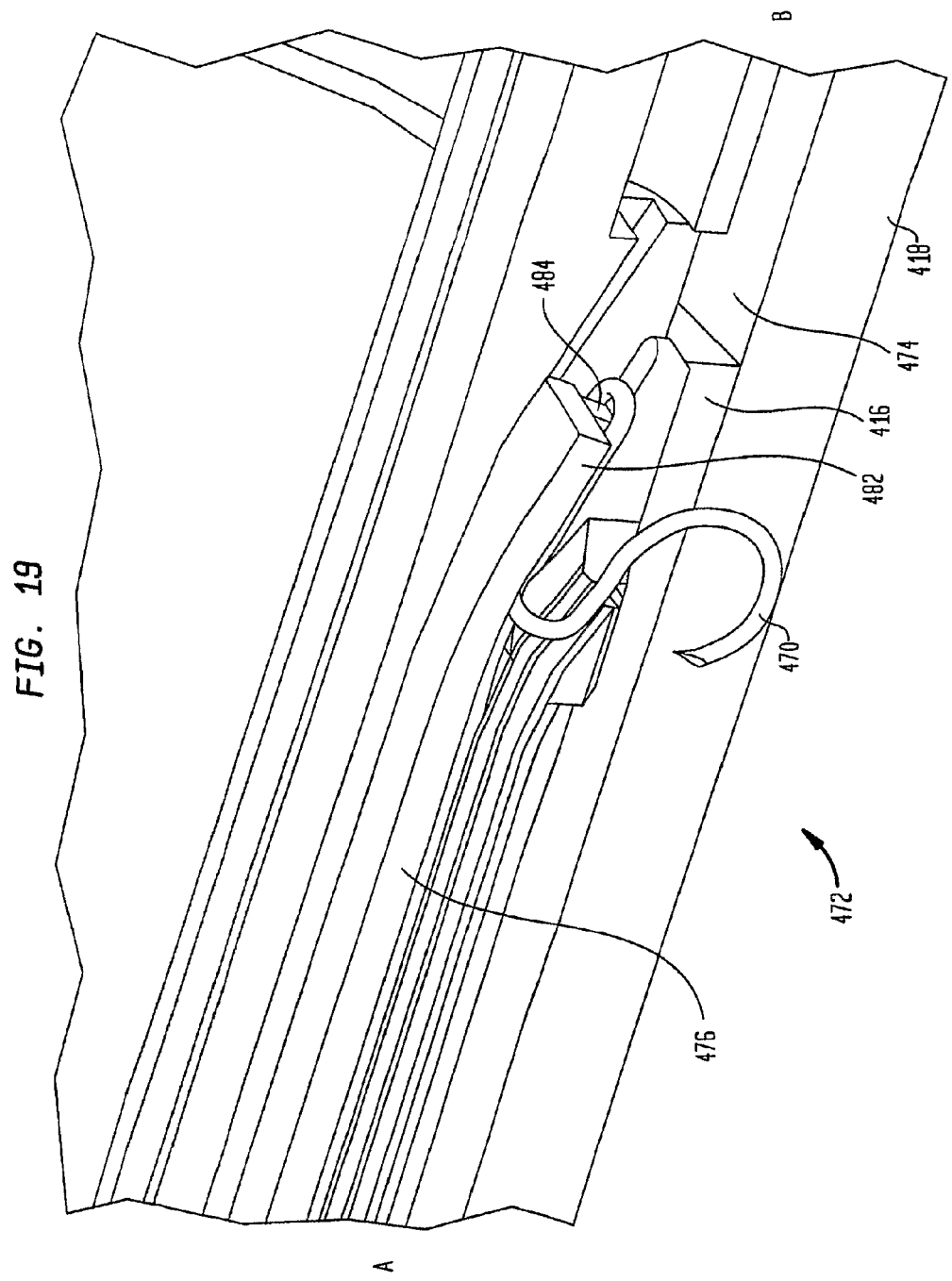

FIG. 19 depicts a further step in the process of firing staple 450 in accordance with one embodiment of the present invention. As shown in FIG. 19, the straight legs 454, 456 of the staple 450 may be permitted by the geometry of the internal staple guide 478 to form back into loops 468, 470 as the staple is pushed away from the stapler body and into the staple exit area 474. The leading spiked ends 458, 460 may penetrate the endograft 416 and the vessel wall 418 as the loops 468, 470 are formed. Formation of such loops 468, 470 preferably secures the endograft 416 to the vessel wall 418. As with previous embodiments, it will be appreciated that a non-compliant balloon or other device may be utilized to ensure that the staple exit area 474 is directly adjacent to the endograft 416 to be stapled, and that the endograft is pressed against the vessel wall 418. In one embodiment, the staples may be pulled (i.e., away from the heart). In another embodiment, the staples may be pushed (i.e., toward the heart) out of the staple cartridge.

Figure 20:
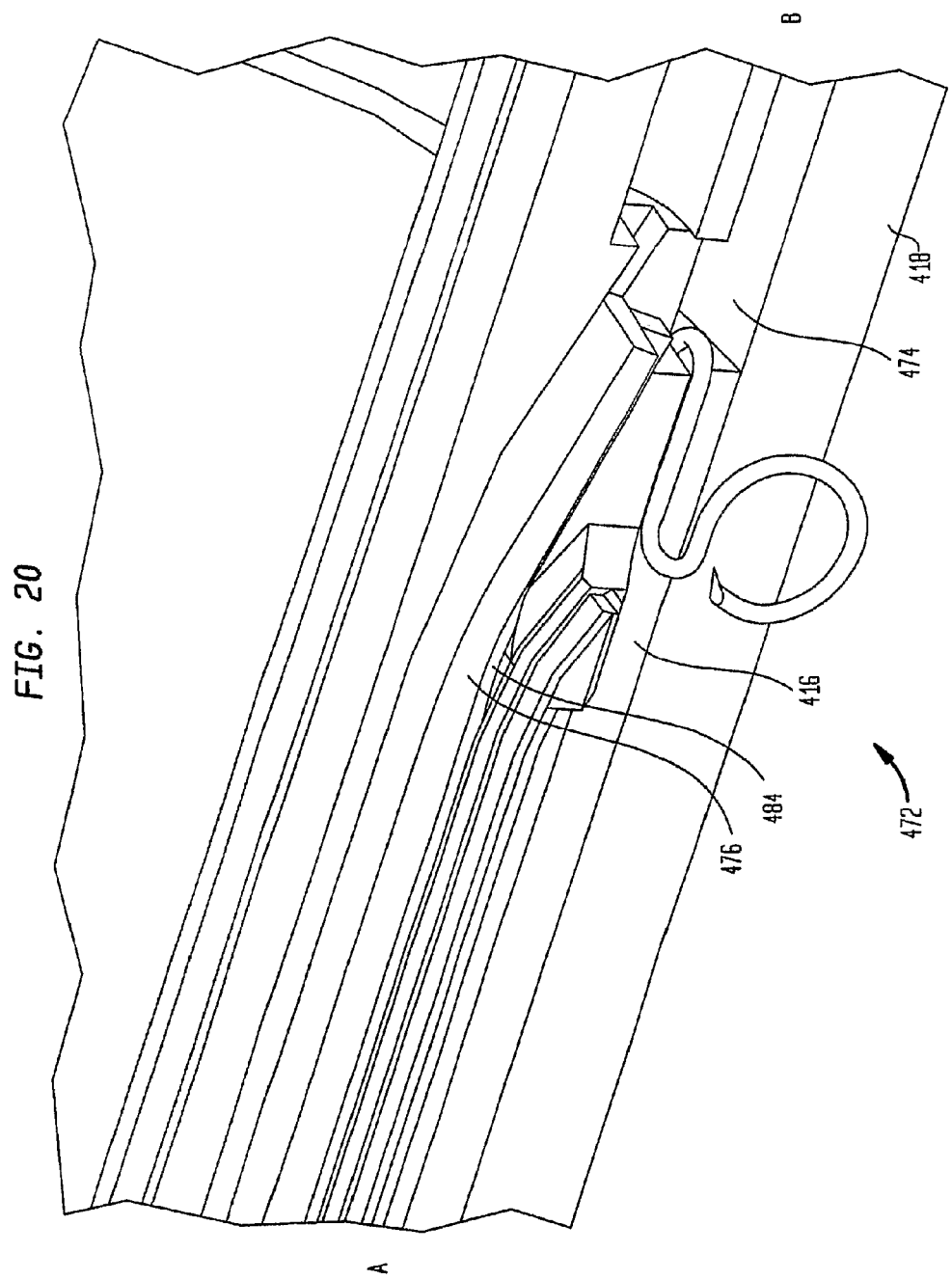
Figure 21:
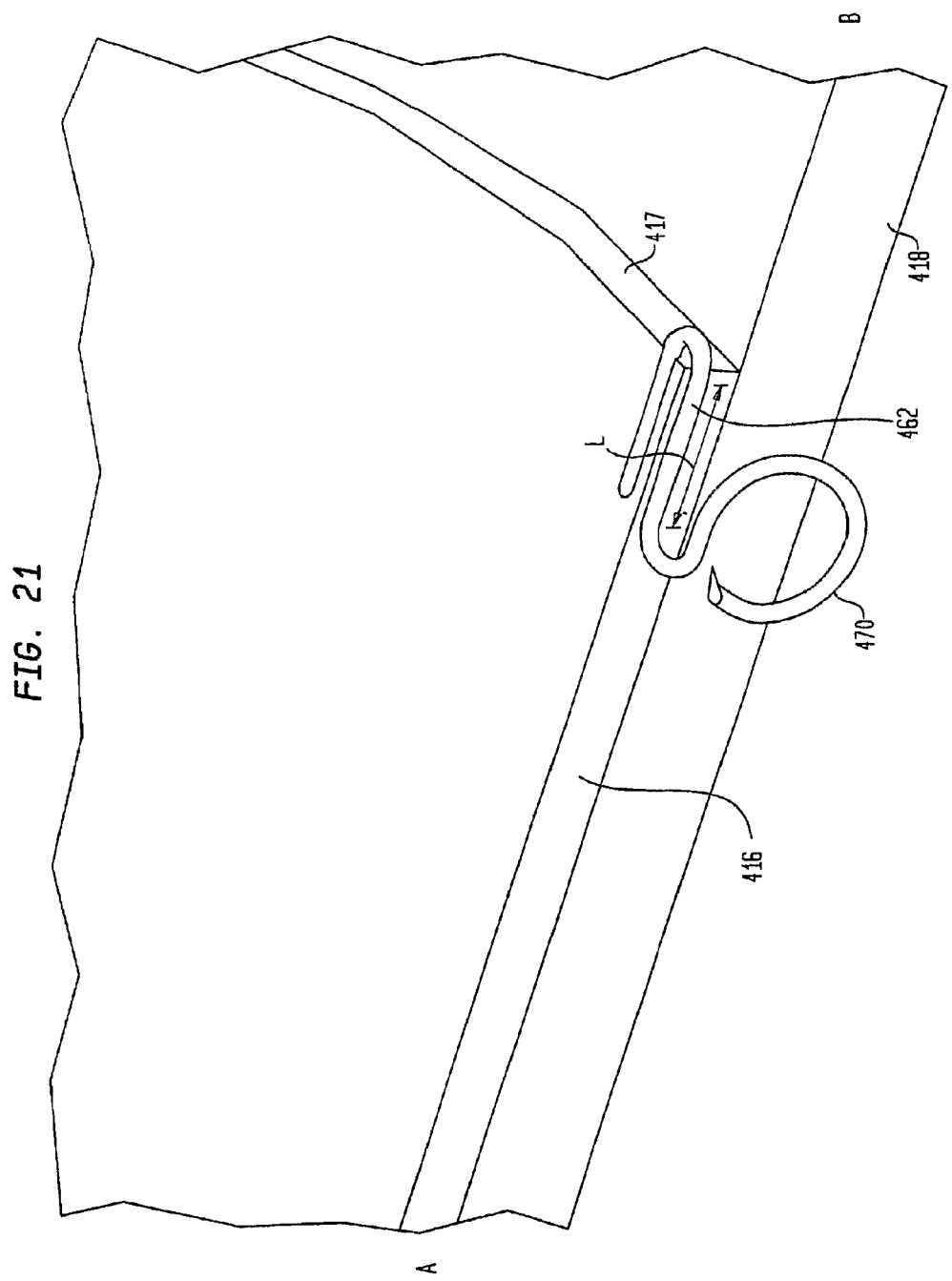
FIG. 21 depicts a cut-away view of the staple of FIG. 17a fired into an endograft and a vessel wall.

A further step in the method of deploying staple 450 is shown in FIG. 20. As shown in FIG. 20, the staple pusher 476 extends into the staple exit area 474, releasing the tongue 462 of the staple 450. The staple 450 is therefore left securing the endograft 416 to the vessel wall 418, as shown in FIG. 21.

As with other embodiments, the diameter of the loops 468, 470 may vary. Staples 450 preselected with a chosen loop diameter may be loaded into the endovascular stapler prior to the surgical procedure. The stapler may be configured with a full-complement of staples of a pre-selected loop diameter. The staples may be color coded to identify the various staple sizes such as "blue" for 3.5 mm, "green" for 4.5 mm, "red" for 7 mm etc. Staples 450 having various sized loops may also be utilized with a single endovascular stapler in which case, the order in which these staples of varying sizes are loaded will be indicated on the actuating handle. The varying loop sizes may affect the excursion required by the pusher 476 to deploy a staple 450, but that is easily remedied by the surgeon in practice. In this regard, each staple length may be associated with a predetermined number of trigger strokes for deployment so the surgeon becomes aware of when the staple is released. Otherwise, visual indication may be provided such as by ultrasound, x-ray, or other known methods.

One feature of staple 450, and those like it having cantilevered tongues, is that the placement of the staple in relation to the edge 417 of the endograft 416 need not be precise. It will be appreciated that deviations from ideal placements may be accommodated by the tongue 462. For example, the tongue 462 includes a length L. Typically, length L is on the order of approximately 1-10 mm, preferably 5 mm. So long as the edge 417 of the endograft 416 is beneath the tongue 462, the placement of the staple 450 should be considered successful. In this regard, the edge 417 of the endograft 416 may be secured beneath the tongue 462, and will not freely open. The tongue 462 will therefore secure any "flapping," or otherwise unsecured portions of the endograft.

Figure 22:
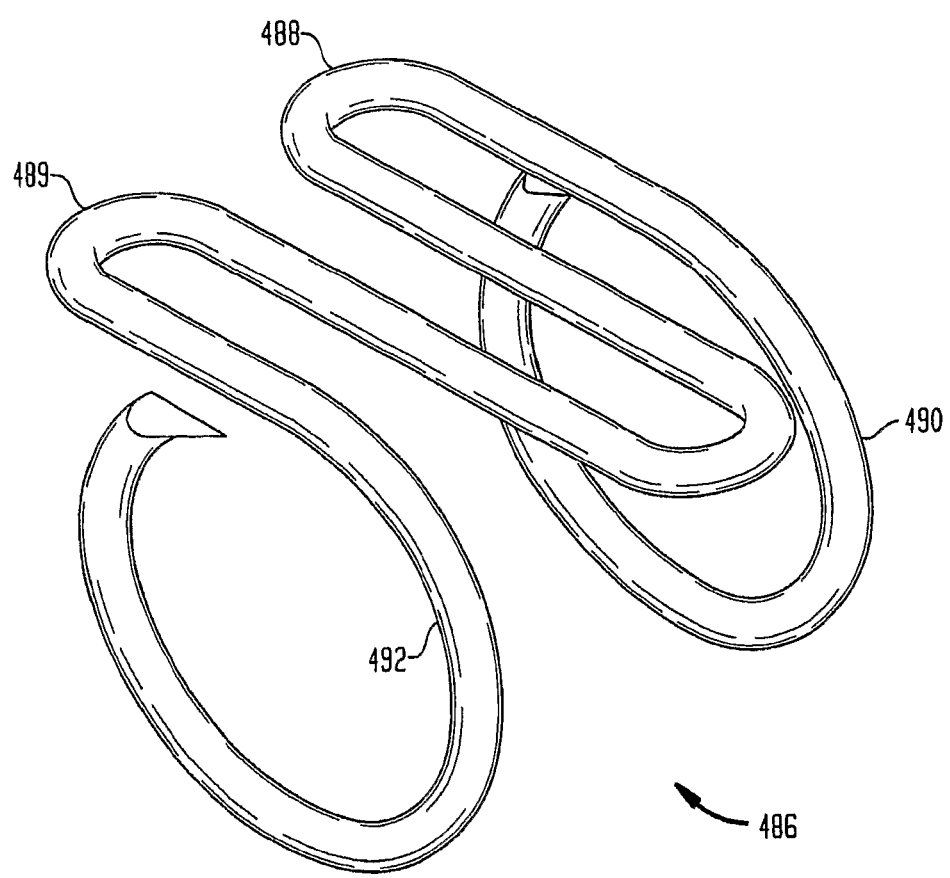
FIG. 22 depicts a perspective view of a fully formed staple following firing by the endovascular stapler in accordance with another embodiment of the present application.

FIG. 22 depicts a perspective view of yet another embodiment of a staple 486 in its natural condition. Staple 486 exhibits many of the advantageous of staple 450 depicted in FIG. 17a, by virtue of its having a pair of tongues 488, 489. Accordingly, staple 486 is capable of applying greater pressure to material trapped between the tongues 488, 489 and the loops 490, 492 by virtue of the added material.

Figure 23:
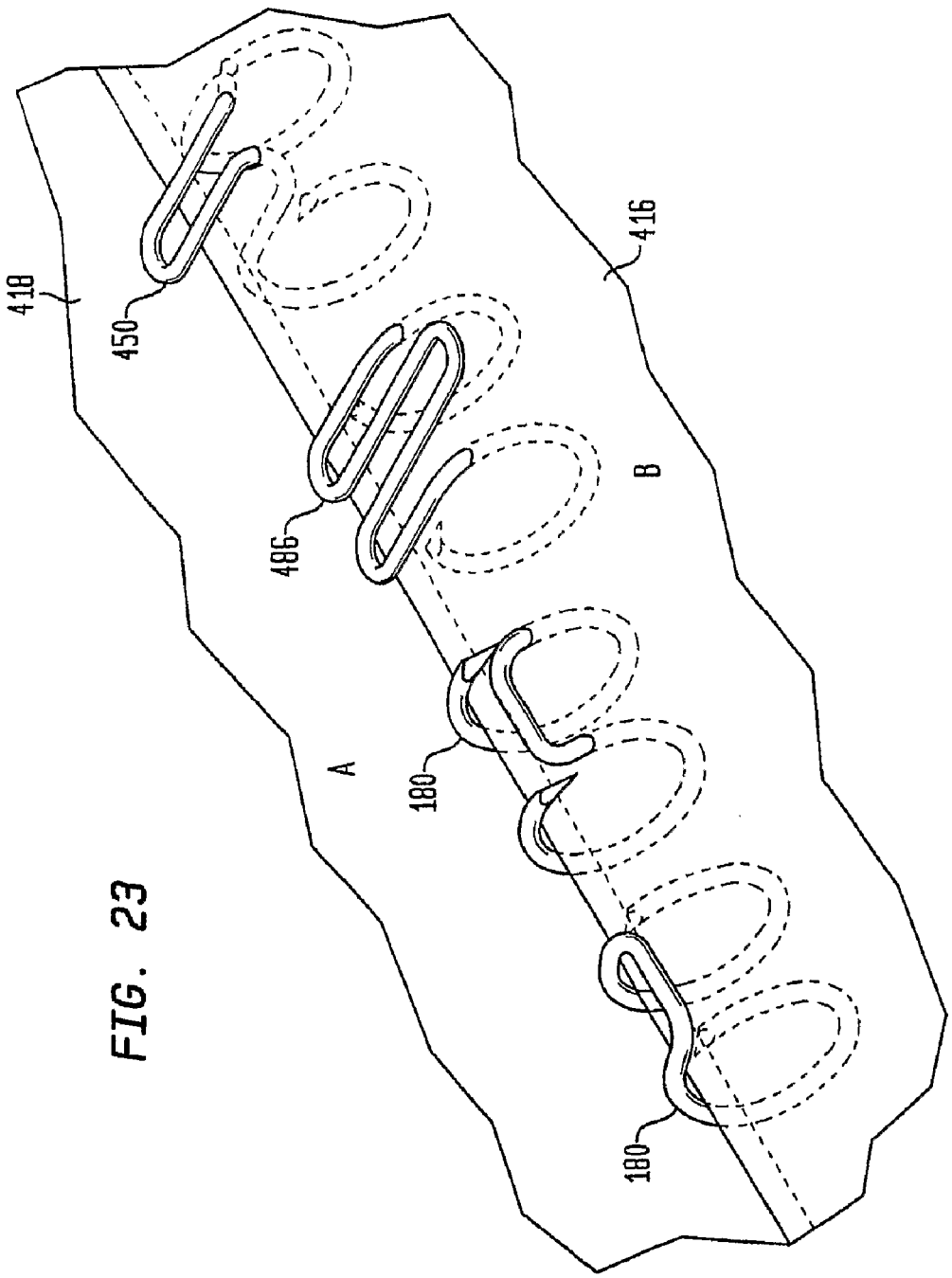
FIG. 23 depicts a perspective view of several staple forms following firing by endovascular staplers in accordance with several embodiments of the present application.

FIG. 23 depicts an array of various embodiments of staples connecting an endograft 416 to a vessel wall 418, including staples 180 as shown in FIG. 8b, staple 450 as shown in FIG. 17b, and staple 486 as shown in FIG. 22. It will be appreciated that the staples shown have been fired from different directions, the two inner staples being fired from a direction corresponding to letter A, near the heart, and the two outer staples being driven from a direction corresponding to letter B, farthest from the heart. Nevertheless, each staple is capable of achieving the desired result in an effective manner. In one embodiment, the staples may be pulled (i.e., away from the heart). In another embodiment, the staples may be pushed (i.e., toward the heart) out of the staple cartridge.

It will be appreciated that the staples shown and otherwise described throughout this may include additional pointed ends, such as three or more. Each of these ends may be connected by a central portion 406. Accordingly, and as an example, a single staple may include a first leg having a pointed end connected to a first central member, a second leg having a pointed end connected on one side to the first central member and on another side to a second central member, and a third leg having a pointed end connected to the second central member, such that the staple forms a W shape with three pointed ends, similar to that found on the head of a trident. It will also be appreciated that the staple legs need not be along the same plane, and may be curved or otherwise angled with respect to each other to conform more closely to the shape of the vessel in which they are intended to be applied. The most limiting factor in determining the number of piercing points, and the curvature of the staple, is practicality of the application.

Figure 24:
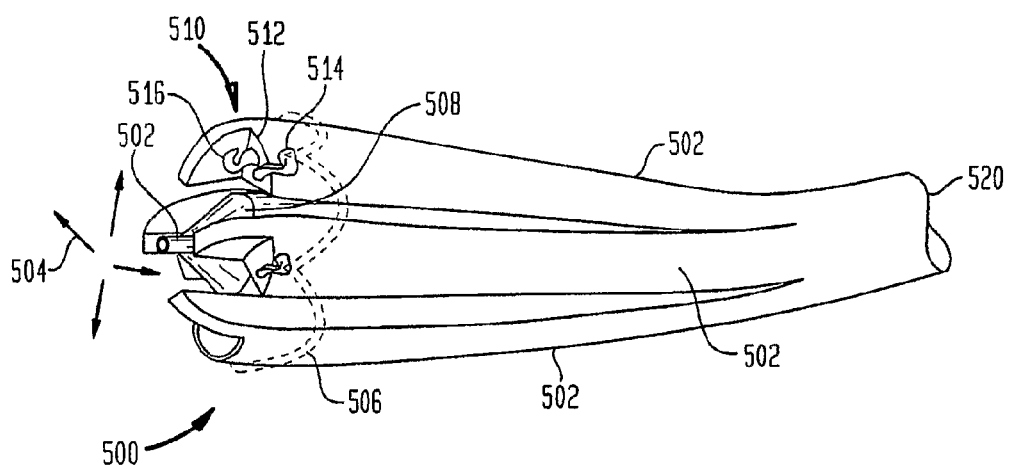
FIG. 24 is a perspective view of a staple housing according to another embodiment of the present application.
Figure 25:
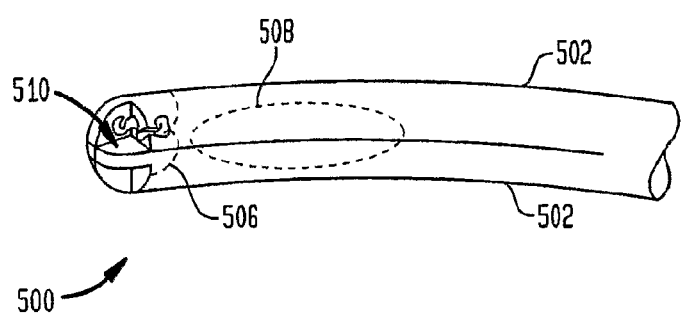
FIG. 25 is a perspective view of the staple housing of FIG. 24 showing the stapler strut members in a retracted position.

FIG. 24 is a perspective view of a staple housing 500 according to another embodiment of the present application. The staple housing 500 can be used with the trigger housing 102 of FIG. 1. The staple housing 500 includes an expandable collet like structure formed from a plurality of expandable portions 502. The expandable portions 502 are shown as single piece arms having a free distal end capable of expanding outwardly from the longitudinal axis of the staple housing as shown by arrow 504. The staple housing 500 is shown in the expanded position and is capable of being in the retracted position as shown in FIG. 25. The staple housing 500 can include an expansion mechanism 506 capable of selectively placing the staple housing 500 in the expanded and retracted position. In one embodiment, the expansion mechanism 506 is an expandable ring or stent disposed in the interior of the staple housing and attached to interior surfaces of the expandable portions 502. The staple housing 500 also includes displacement mechanism 508 disposed within an interior surface of the staple housing and adapted to push the expandable portions 502 further outward and to help maintain the expandable portions in the expanded position. In one embodiment, the displacement mechanism 508 can be a balloon adapted to be selectively inflated and deflated. In one embodiment, the balloon can be a partially compliant balloon such as the balloon of the staple housing of the present application described above.

Each of the expandable portions 502 includes a staple cartridge 510 adapted to store and discharge at least one staple 512 to secure an endograft to a vessel. The staple 512 has a back end 514 extending away from the center of the staple housing 500 configured for attaching to an end portion of an endograft (not shown). In one embodiment, the endograft can be attached to the staple housing during insertion of the staple housing into the vessel as a single unit. The staple 512 also has a front end 516 extending toward the center of the staple housing configured for securing an endograft to a vessel (not shown) when the staple is discharged. The staple housing 500 includes a catheter portion 520 having channels and wires similar to those of catheter 106 of the stapler 100 of FIG. 1.

In operation, an actuator wire can be used to actuate the expansion mechanism 506 which causes the expandable portions 502 to expand outward. Next, an inflation channel can be used to inflate the balloon 508 which pushes the expandable portions 502 further outward and helps maintain the expandable portions in the expanded position. Once inflated, a staple actuator mechanism can be used to discharge the staples 512 from the staple cartridges 510. As the staples 512 exit the staple cartridges, the staples rotate such that the front end 516 of the staples secures the endograft to the vessel and the back end 514 detaches itself from the endograft. In this manner, the endograft is secured to the vessel and the staple housing can be retracted for another discharge application or for complete withdrawal from the vessel.

The staple housing 500 is shown with four expandable portions 502, with each portion including one staple cartridge 510 for a total of four staple firing ports. It will therefore be appreciated that the housing 500 may discharge four staples at once. In a preferred embodiment, eight staples can be utilized to secure a graft. This can be accomplished by actuating the staple housing once, rotating the staple housing to another position, and then actuating the staple housing again. In this regard, each staple cartridge 510 may include at least two staples arranged in tandem for subsequent discharge.

In another embodiment, each expandable portion 502 may include a plurality of staple cartridges. For example, the staple cartridges may be stacked longitudinally along the longitudinal axis of the staple housing. When so oriented, the staple housing may be fired once to deploy the initial set of staples, then advanced until the lower staple cartridge aligns with the previously fired staples, rotated, and fired.

The staple housing 500 is shown with four expandable portions 502, however, a different number of expandable portions can be used such as 2, 3, 5, 6 or other number based on desired requirements. The components of the staple housing 500 including the expandable portions 502 can be made of material similar to that of the stapler 100 of FIG. 1.

FIG. 25 is a perspective view of the staple housing 500 of FIG. 24 showing the staple housing in the retracted position. The expandable portions 502 can be retracted by deflating the balloon 508 and releasing the tension on the expansion mechanism 506 using techniques similar to those described above.

Figure 26:
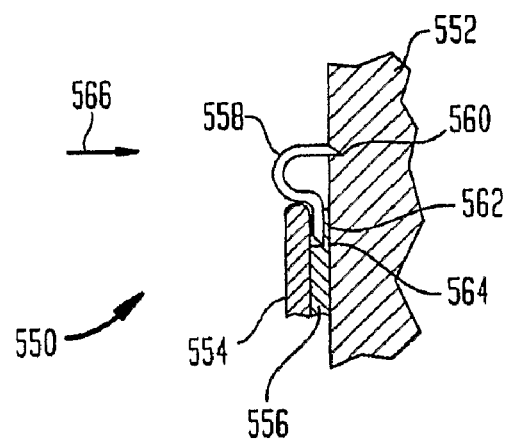
FIG. 26 is a partial longitudinal sectional view of a staple cartridge in accordance with an embodiment of the present application.

FIG. 26 is a partial cross-sectional view of a staple cartridge capable of being used with the staple housing of FIG. 24 in accordance with an embodiment of the present application. The staple cartridge 550 is disposed in a vessel (not shown) and abuts a side surface of an endograft 552. The staple cartridge 550 includes a staple forming element 554 and a staple holder element 556. The staple cartridge 550 stores a staple 558 which can be discharged into the endograft 552 to secure the endograft to a vessel. The staple 558 may be anvil-less and discharged at an angle of 90°, shown as arrow 566, from a longitudinal axis of the staple cartridge 550. The staple 558 includes a first end 560 with a pointed portion for insertion into the endograft. The staple 558 includes a second end 562 which fits in a recess 564 of the staple holder element 556 to hold the staple in place during the discharge process.

Figure 27:
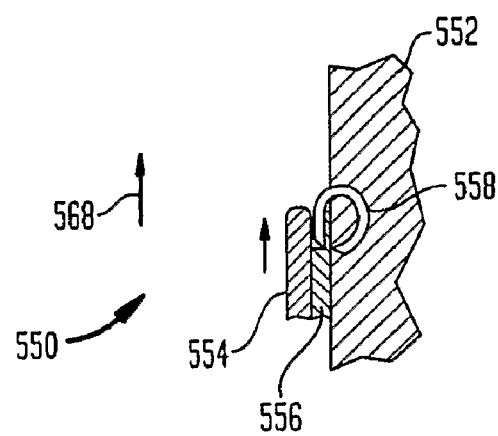
FIG. 27 shows the staple cartridge of FIG. 26 discharging a staple.

FIG. 27 shows the staple cartridge 550 of FIG. 26 discharging the staple 558 into the endograft 552. In one embodiment, the staple forming element 554 is advanced in the upward direction, shown by arrow 568, which causes the staple forming element 554 to form the staple 558 as shown. In other words, the staple holding element 556 may remain stationary while the staple forming element 554 is pulled upward to push portions of the staple 558 against the staple forming element such that the first end 560 of the staple is pushed through the endograft and into the vessel. In another embodiment, the staple 558 may be pulled downward (opposite to direction shown by arrow 568) against the staple forming element 554 in order to form the staple. In this case, the staple forming element 554 may remain stationary while the staple holder element 556 is pulled down to push portions of the staple against the staple forming element such that the first end 560 of the staple 558 is pushed through the endograft and into the vessel.

Figure 28:
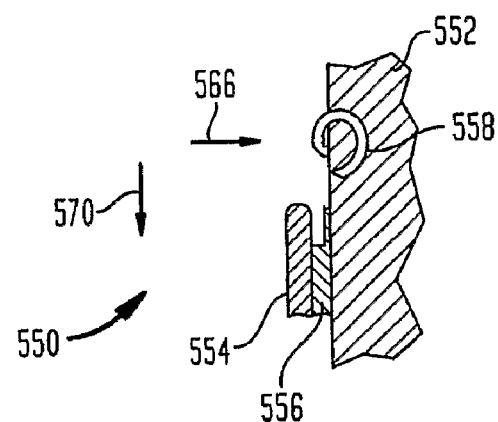
FIG. 28 shows the staple cartridge of FIG. 27 fully discharging a staple.

FIG. 28 shows the staple cartridge of FIG. 27 with the staple 558 fully discharged into the endograft 552. Once formed, the staple 558 is discharged into the endograft and vessel in the direction shown by arrow 566. Once discharged, the staple cartridge and associated staple housing may be withdrawn in a direction shown by arrow 570. In other embodiments, the staple can be deployed by pushing the staple, rather than pulling as demonstrated by the above-mentioned aspects of the present application.

Figure 29:
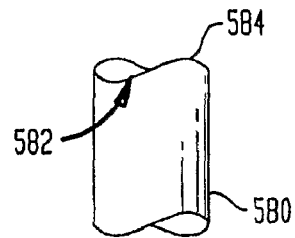
FIG. 29 is a perspective view of an endograft in accordance with an embodiment of the present application.
Figure 30:
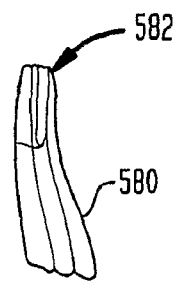
FIG. 30 shows the endograft of FIG. 29 in a collapsed condition.

FIG. 29 is a perspective view of an endograft 580 in an expanded position in accordance with an embodiment of the present application. FIG. 30 shows the endograft of FIG. 29 in a retracted position. The endograft 580 may include a radial support mechanism 582 at its proximal end 584. The radial mechanism 582 may allow for initial sealing of the endograft to a vessel (not shown). In a preferred embodiment, the radial support mechanism 582 can be a flexible ring or stent. The ring or stent may be made from super-elastic metal or stainless steel, and may be configured to spring back into its natural shape when permitted. In one embodiment, the radial support mechanism 582 may permit a staple housing to attach the endograft to the exterior surfaces of the staple housing. In this manner, the staple housing and the endograft can be inserted into a vessel as a single unit.

Figure 31:
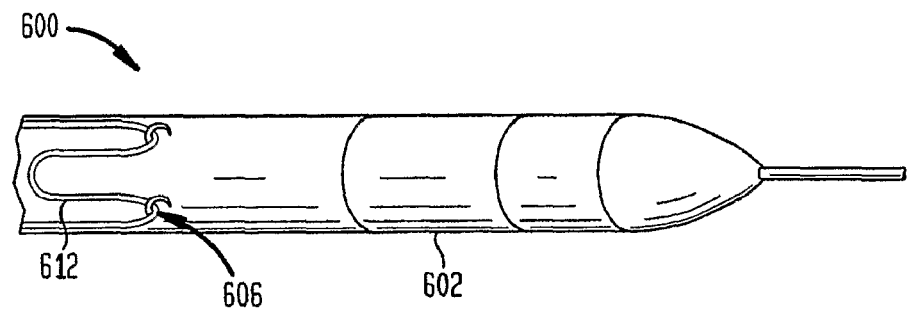
FIG. 31 is a perspective view of a staple housing in accordance with another embodiment of the present application.

FIG. 31 is a perspective view of a staple housing 600 in accordance with another embodiment of the present application. The staple housing 600 can be used with stapler 100 of FIG. 1. In addition, the staple housing 600 includes expandable portions 602 capable of expanding and retracting similar to the expandable portions of the staple housing 104 (FIG. 4) of the present application described above. However, unlike structure of the staple housing 104, the staple housing 600 includes an endograft capture fastener 606 adapted to capture an endograft 612 during installation of the staple housing 600 in a vessel. In this regard, the staple housing 600 and endograft 612 may be inserted into a vessel as a single unit. FIG. 31 shows the staple housing 600 in a retracted position whereas FIG. 32 shows the staple housing in an expanded position.

Figure 32:
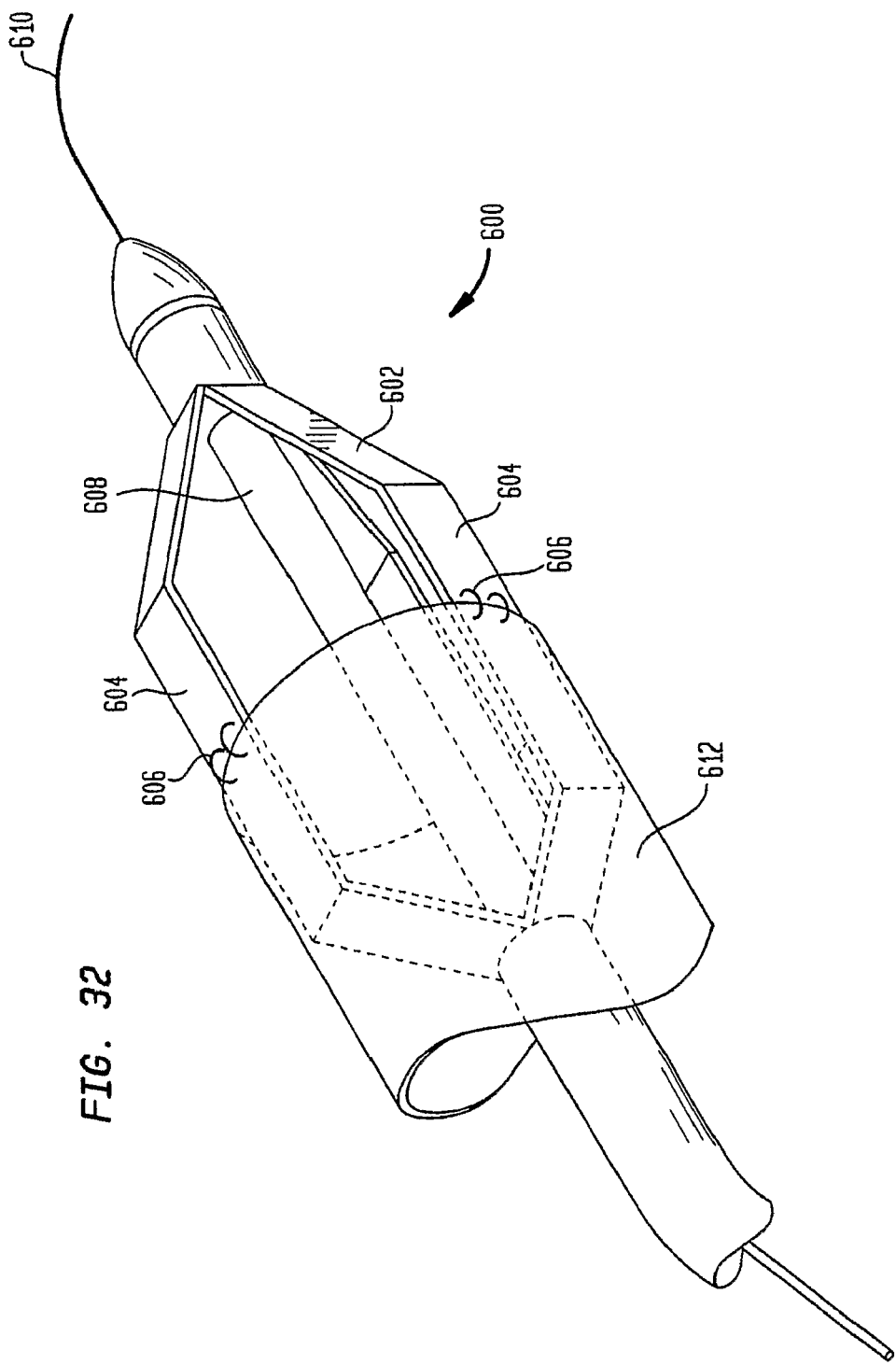
FIG. 32 shows the stapler strut members of FIG. 31 in an expanded condition.

FIG. 32 shows the staple housing 600 of FIG. 31 in an expanded position. To expand the staple housing 600, expandable portions 602 are expanded outward using techniques such as those previously discussed. The expandable portions 602 may each have a staple cartridge 604 for supporting the endograft retention mechanism 606. The staple housing 600 may also include a catheter lumen 608 for carrying a guide wire 610 for insertion into a vessel (not shown).

In one embodiment, the endograft capture fastener 606 comprises a staple such as staple 512 of staple housing 500 of FIG. 24. In addition, the endograft retention mechanism 606 is a fastener such as staple which may be discharged in a manner similar to that described above in the context of staple housing 500 of FIG. 24. The discharge of the capture mechanism 606 causes the endograft 612 to be secured to the vessel (not shown). In addition, the capture mechanism 606 is released by the staple housing such that the housing may be withdrawn from the vessel with the endograft 612 attached thereto.

Figure 33:
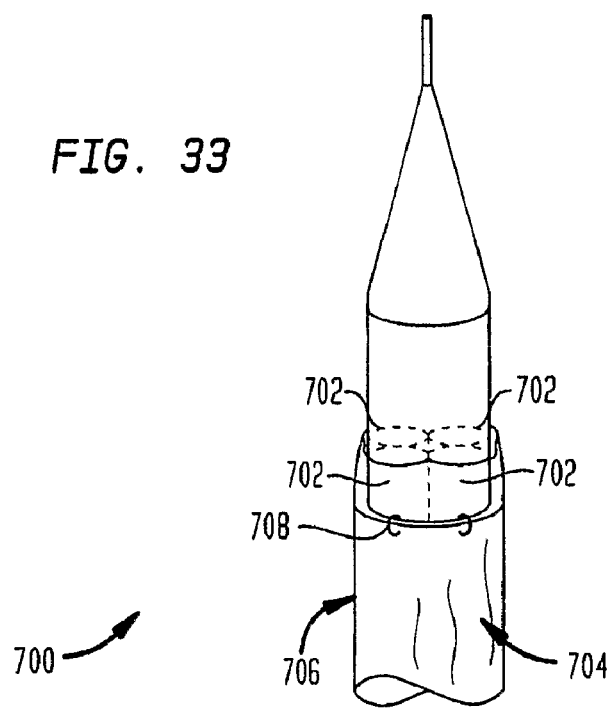
FIG. 33 is a perspective view of a stapler in accordance with yet another embodiment of the present application.

FIG. 33 is a perspective view of staple housing in accordance with yet another embodiment of the present application. The staple housing 700 is capable of being expanded without the use of an interior located displacement mechanism such as a balloon previously described above. The staple housing 700 includes a plurality of expandable portions 702 each having a staple cartridge 720 (shown in FIG. 35) for supporting an endograft retention mechanism 708 similar to the mechanism of the staple housing 600 of FIG. 32. The endograft retention mechanism 708 is attached to an endograft 704. The staple housing 700 may include a catheter sheath 706 which covers the endograft 704 and may retain the staple housing in a contracted position.

Figure 34:
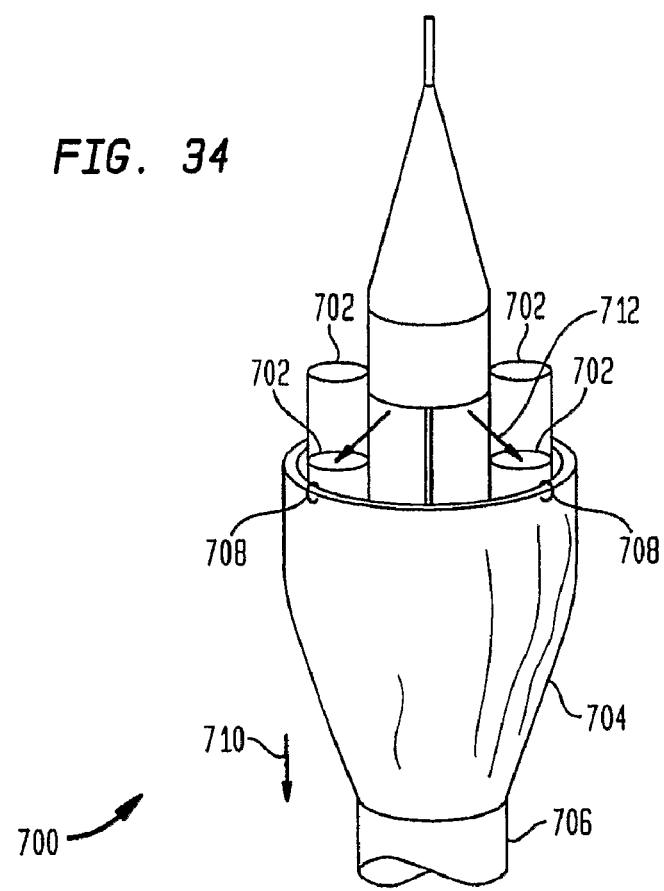
FIG. 34 shows the stapler units (strut members) of FIG. 33 in an expanded condition.

FIG. 34 shows the staple housing of FIG. 33 in an expanded position. The sheath 706 may be pulled in a downward direction, shown by arrow 710, along a portion of the length of the staple housing 700 to allow the staple housing to expand outward direction, shown by arrows 712, thus sealing a portion of the endograft 704 against a vessel wall (not shown).

Figure 35:
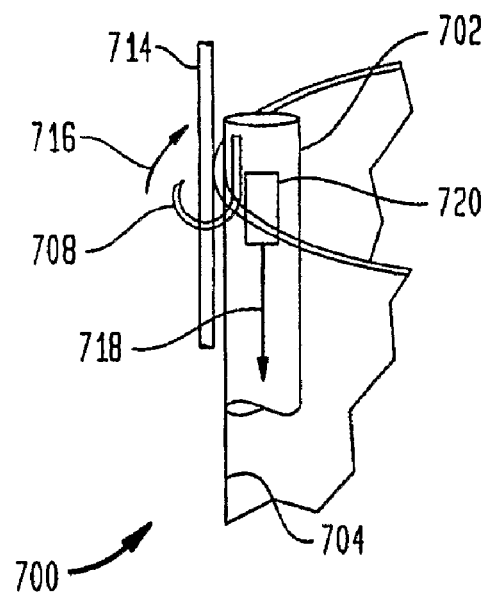
FIG. 35 is a detailed view of a staple cartridge of FIG. 34 showing a staple being discharged.

FIG. 35 is a detailed view of the staple cartridge of FIG. 34. The expanding portion 702 may include a staple cartridge 720 with an actuator (not shown) to discharge the graft retention mechanism 708. To discharge the mechanism 708, the actuator is moved in a downward direction, shown by arrow 718, which causes the mechanism to rotate in the direction shown by arrow 716.

Figure 36:
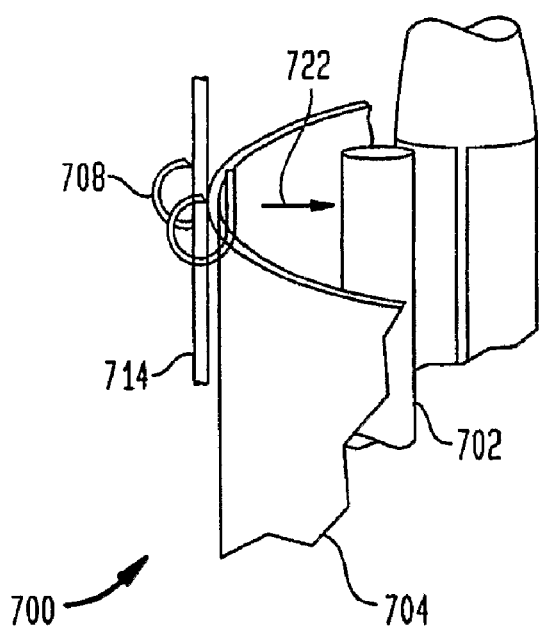
FIG. 36 is another view of the staple cartridge of FIG. 35 showing a staple discharged and the unit (strut member) retracted.

FIG. 36 is another view of the staple cartridge of FIG. 35. As the retention mechanism 708 rotates, it pierces the vessel wall 714 thereby securing the endograft 704 to the vessel wall. Once the mechanism 708 is discharged, the expandable portions 702 retract in an inward direction, shown by arrow 722, towards the center of the staple housing. The endograft is secured to the vessel wall and the staple housing 700 can now be withdrawn.

FIGS. 37a-37b to 41a-41b depict various staples in accordance with other embodiments of the present application. The staples are capable of being used with the techniques of the present application. Preferably, the staples are constructed of a memory alloy such as Nitinol, as is commonly used in the art. The staples can be laser cut from sheets of memory alloy which can provide a relatively easy means of manufacture.

Figure 37A:
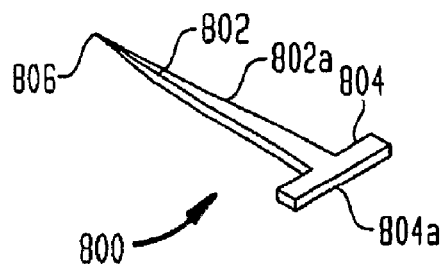
FIG. 37a depicts a perspective view of a single prong staple capable of being utilized with an endovascular stapler in accordance with a still further embodiment of the present application.
Figure 37B:
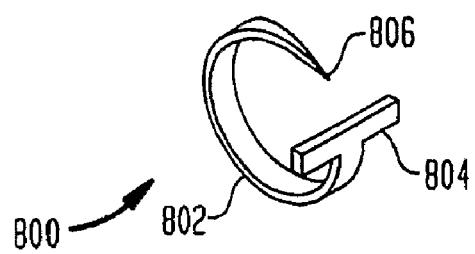
FIG. 37b depicts a perspective view of the staple shown in FIG. 37a following firing by the endovascular stapler.

FIG. 37a is a perspective view of a staple 800 and FIG. 37b shows the staple 800 following firing by an endovascular stapler. The condition shown in FIG. 37b is the natural condition of the staple 800 showing the generally loop shape of the staple. Within the staple housing of an endovascular stapler, the staple 800 will typically be deformed into the condition shown in FIG. 37a. As shown in FIG. 37a, the staple 800 may be generally T-shaped comprising a head portion 804 having a generally rectangular shape with a top surface 804a and a leg portion 802 with a top surface 802a. The leg 802 extends from a mid point of the head 804 with the top surface 802a of the leg being on the same plane as the top surface 804a of the head 804. The leg 802 preferably terminates with a spiked end 806.

Figure 38A:
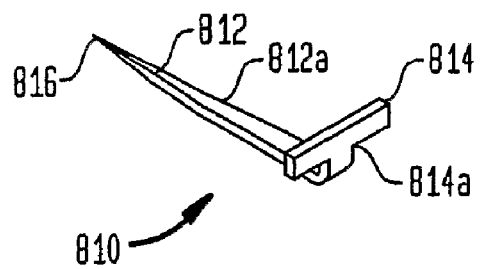
FIG. 38a depicts a perspective view of another staple type capable of being utilized with an endovascular stapler in accordance with a still further embodiment of the present application.
Figure 38B:
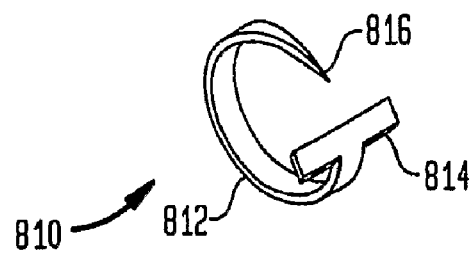
FIG. 38b depicts a perspective view of the staple shown in FIG. 38a following firing by the endovascular stapler.

FIG. 38a is a perspective view of a staple 810 and FIG. 38b shows the staple 810 following firing by an endovascular stapler. The condition shown in FIG. 38b is the natural condition of the staple 810 showing the generally loop shape of the staple. Within the staple housing of an endovascular stapler, the staple 810 will typically be deformed into the condition shown in FIG. 38a. As shown in FIG. 38a, the staple 810 may be generally T-shaped comprising a head portion 814 having a generally rectangular shape with a top surface 814a and a leg portion 812 with a top surface 812a. The leg 812 extends from a mid point of the head 814 with the top surface 812a of the leg perpendicular to the top surface 814a of the head 814. The leg 812 preferably terminates with a spiked end 816.

Figure 39A:
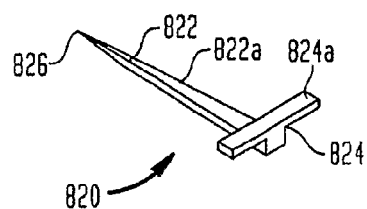
FIG. 39a depicts a perspective view of yet another staple type capable of being utilized with an endovascular stapler in accordance with a still further embodiment of the present application.
Figure 39B:
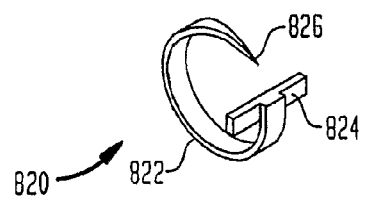
FIG. 39b depicts a perspective view of the staple shown in FIG. 39a following firing by the endovascular stapler.

FIG. 39a is a perspective view of a staple 820 and FIG. 39b shows the staple 820 following firing by an endovascular stapler. The condition shown in FIG. 39b is the natural condition of the staple 820 showing the generally loop shape of the staple. Within the staple housing of an endovascular stapler, the staple 820 will typically be deformed into the condition shown in FIG. 39a. As shown in FIG. 39a, the staple 820 may be generally T-shaped comprising a head portion 824 having a generally rectangular shape with a top surface 824a and a leg portion 822 with a top surface 822a. The head 824 is disposed over the leg 822 in a stacked manner with the top surface 822a of the leg being on a different plane than the top surface 824a of the head 824. The leg 822 preferably terminates with a spiked end 826.

Figure 40A:
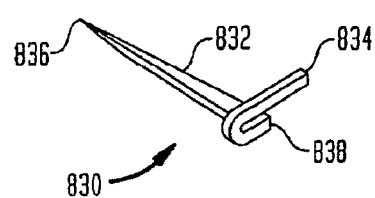
FIG. 40a depicts a perspective view of a staple capable of being utilized with an endovascular stapler in accordance with a still further embodiment of the present application.
Figure 40B:
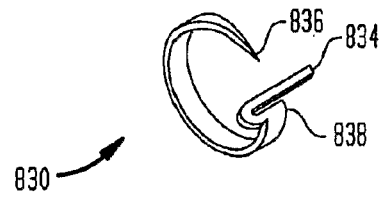
FIG. 40b depicts a perspective view of the staple shown in FIG. 40a following firing by the endovascular stapler.

FIG. 40a is a perspective view of a staple 830 and FIG. 40b shows the staple 830 following firing by an endovascular stapler. The condition shown in FIG. 40b is the natural condition of the staple 830 showing the generally loop shape of the staple. Within the staple housing of an endovascular stapler, the staple 830 will typically be deformed into the condition shown in FIG. 40a. As shown in FIG. 40a, the staple 830 may be generally T-shaped comprising a head portion 834 having a generally rectangular shape with a top surface 834a and a leg portion 832 with a top surface 832a. A bent portion 838 extends between the head 834 and the leg 832. The leg 832 preferably terminates with a spiked end 836.

Figure 41A:
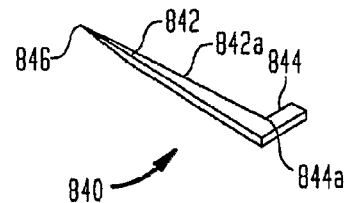
FIG. 41a depicts a perspective view of a staple capable of being utilized with an endovascular stapler in accordance with a still further embodiment of the present application.
Figure 41B:
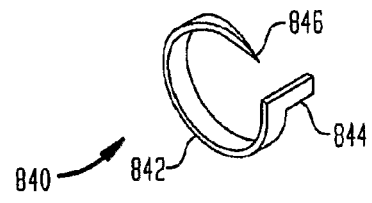
FIG. 41b depicts a perspective view of the staple shown in FIG. 41a following firing by the endovascular stapler.

FIG. 41a is a perspective view of a staple 840 and FIG. 41b shows the staple 840 following firing by an endovascular stapler. The condition shown in FIG. 41b is the natural condition of the staple 840 showing the generally loop shape of the staple. Within the staple housing of an endovascular stapler, the staple 840 will typically be deformed into the condition shown in FIG. 41a. As shown in FIG. 41a, the staple 840 may be generally L-shaped comprising a head portion 844 with a top surface 844a and a leg portion 842 with a top surface 842a. The leg 842 and the head 844 are arranged in a manner such that the top surface head 844a of the head is on the same plane as the top surface 842a of the leg. The leg 842 preferably terminates with a spiked end 846.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An endovascular stapler system for securing an endograft to a vessel, said system comprising:
   a plurality of staple cartridges each including staples formed from a memory alloy and an exit area for discharge of said staples therethrough, each of said staples including first and second legs joined by a central portion, said lees forming two parallel loops when in a natural condition each of said staples having two parallel straight legs joined by said central portion when in said deformed condition, said staples being in a deformed condition while in said plurality of staple cartridges;

a staple housing including an internal staple guide having an arcuate path defined by flanges and limits of said internal staple guide, said plurality of staple cartridges being positioned in said staple housing, said internal staple guide being configured to receive said staples and maintain said staples in a deformed condition while said staples are contained within said housing, an actuating assembly adapted for actuating said plurality of staple cartridges for discharging said staples along said arcuate path and through said exit area; and an expansion mechanism in operative association with said plurality of staple cartridges, said expansion mechanism operative for pushing said exit area against said endograft when discharging said staples therethrough.

2. The endovascular stapler of claim 1, wherein said expansion mechanism comprises a plurality of expandable portions.

3. The endovascular stapler of claim 2, wherein said plurality of expandable portions comprises strut members configured to form an expandable cage structure.

4. The endovascular stapler of claim 3, wherein each strut member comprises a plurality of strut segments each coupled to each other using a hinge mechanism.

5. The endovascular stapler of claim 4, wherein each strut member is coupled to a staple cartridge.

6. The endovascular stapler of claim 3, wherein each strut member is coupled to the staple housing a hinge mechanism.

7. The endovascular stapler of claim 6, wherein the hinge mechanism is a living hinge.

8. The endovascular stapler of claim 2, wherein said expandable portions are adapted to expand outwardly away from a longitudinal axis of said stapler.

9. The endovascular stapler of claim 2, wherein said expandable portions are adapted to retract inwardly toward a longitudinal axis of said stapler.

10. The endovascular stapler of claim 1, wherein said plurality of staple cartridges are adapted to be actuated in a substantially simultaneous manner.

11. The endovascular stapler of claim 1, wherein said plurality of staple cartridges are adapted to be actuated in a sequential manner, with one staple cartridge being actuated after another staple cartridge being actuated.

12. The endovascular stapler of claim 1, wherein said actuating assembly comprises a pusher and a trigger, said pusher adapted to be advanced by said trigger to discharge said at least one staple.

13. The endovascular stapler of claim 12, wherein said pusher advances said staples in a direction opposite to a distal end of said staple housing.

14. The endovascular stapler of claim 1, at least one of said staples cartridges includes a plurality of staples therein.

15. The endovascular stapler of claim 14, wherein said staples are arranged in a tandem manner.

16. The endovascular stapler of claim 1, wherein at least one of said staples is deformed prior to exiting said exit area.

17. The endovascular stapler of claim 1, further comprising a displacement mechanism in operative association with said plurality of staple cartridges, wherein said displacement mechanism is operative for pushing said staple cartridges against said endograft.

18. The endovascular stapler of claim 17, wherein said displacement mechanism comprises a balloon positioned to exert pressure on said staple cartridges.

19. The endovascular stapler of claim 17, wherein said balloon is adapted to be selectively inflated and deflated.

20. The endovascular stapler of claim 17, wherein said balloon is a partially compliant balloon.

21. The endovascular stapler of claim 17, wherein at least a portion of said balloon is disposed within an interior of said staple housing.

22. The endovascular stapler of claim 17, wherein said balloon comprises a plurality of segments wherein at least one of said segments is operatively coupled to at least one of said plurality of staple cartridges.

23. The endovascular stapler of claim 22, wherein at least one of said segments is in fluid communication with at least another of said segments.

24. The endovascular stapler of claim 22, wherein at least one of said segments is adapted to engage at least a portion of said endograft.

25. The endovascular stapler of claim 22, wherein at least one of said segments is attached to a surface opposite said exit area of at least one of said plurality of staple cartridges.

26. The endovascular stapler of claim 22, wherein said segments are spaced apart to provide at least one opening therebetween.

27. The endovascular stapler of claim 26, wherein said opening is adapted to allow flow of a fluid or gas therethrough.

28. The endovascular stapler of claim 17, wherein said displacement mechanism comprises a stent.

29. The endovascular stapler of claim 28, wherein said stent is adapted to expand outwardly away from a longitudinal axis of said stapler.

30. The endovascular stapler of claim 28, wherein said stent is adapted to retract inwardly toward a longitudinal axis of said stapler.

* * * * *